(12) United States Patent
Zhang et al.

(10) Patent No.: US 12,139,557 B2
(45) Date of Patent: Nov. 12, 2024

(54) SYNTHETIC PEPTIDE SP2 AND APPLICATION THEREOF

(71) Applicant: TAIAN CITY QIHANG BIOTECHNOLOGY CO., Shandong (CN)

(72) Inventors: Wanqin Zhang, Shandong (CN); Yintian Li, Shandong (CN); Xuewen Ji, Shandong (CN); Limei Zhao, Shandong (CN)

(73) Assignee: TAIAN CITY QIHANG BIOTECHNOLOGY CO., Shandong (CN)

(*) Notice: Subject to any disclaimer, the term of this patent is extended or adjusted under 35 U.S.C. 154(b) by 0 days.

(21) Appl. No.: 17/809,940

(22) Filed: Jun. 30, 2022

(65) Prior Publication Data

US 2022/0389060 A1     Dec. 8, 2022

Related U.S. Application Data

(63) Continuation of application No. 17/056,414, filed as application No. PCT/CN2018/115567 on Nov. 17, 2018, now abandoned.

(30) Foreign Application Priority Data

Nov. 9, 2018 (CN) ......................... 201811333589.1

(51) Int. Cl.
     *C07K 7/08*      (2006.01)
     *A61P 35/00*      (2006.01)
     *A61P 35/02*      (2006.01)
     *A61K 38/00*      (2006.01)

(52) U.S. Cl.
     CPC ................ *C07K 7/08* (2013.01); *A61P 35/00* (2018.01); *A61P 35/02* (2018.01); *A61K 38/00* (2013.01)

(58) Field of Classification Search
     None
     See application file for complete search history.

(56) References Cited

U.S. PATENT DOCUMENTS 6,126,939 A     10/2000    Eisenbach-Schwartz et al.
2021/0261618 A1*   8/2021    Zhang ..................... C07K 7/08

FOREIGN PATENT DOCUMENTS

CN        103819554 A     5/2014
WO    WO 2020093427   *   5/2020

OTHER PUBLICATIONS

GenBank Accession No. AMX81493.1, Apr. 13, 2016.
GenBank Accession No. D9U2B5.1, Nov. 22, 2017.
NCBI BLAST search seq id 1 (retrieved from https://blast.ncbi.nlm.nih.gov/Blast.cgi on Oct. 28, 2021, 15 pages) (Year: 2021).

* cited by examiner

*Primary Examiner* — Ronald T Niebauer
(74) *Attorney, Agent, or Firm* — NKL Law; Allen Xue

(57) ABSTRACT

A synthetic peptide sp2 has the amino acid sequence shown in SEQ ID No: 1. sp2 has obvious anti-tumor growth activity on xenograft tumours such as subcutaneous human pancreatic cancer, human cervical cancer, and human ovarian cancer in nude mice, with a dose-effect and time-effect relation; and has the effect of delaying metastasis and prolonging the survival time of nude mouse having in situ transplantation of human pancreatic cancer and lung adenocarcinoma. After the animals were given intravenous injection of sp2 at a dose of 2000 mg/kgBW, no toxicity reaction and death were observed. The applications of sp2 also include: (1) preventing and/or treating of tumor; (2) inhibiting proliferation and/or growth and/or invasion of tumor cells; (3) enhancing the anti-tumor immune response; (4) inducing tumor cell differentiation; (5) preparing anti-tumor drugs; (6) inhibiting tumor telomerase activity; and (7) regulating the tumor cell cycle.

2 Claims, 21 Drawing Sheets

Specification includes a Sequence Listing.

VIS 1 Results

| Pk# | RT | Name | Height | Area | ESTD Conc/nmol | Calc% |
|---|---|---|---|---|---|---|
| 1 | 4.927 | Asp | 111278 | 1709263 | 1.298 | 172.803 |
| 3 | 7.007 | Glu | 393602 | 8007624 | 5.381 | 791.502 |
| 4 | 9.893 | Gly | 81850 | 1570317 | 1.271 | 95.478 |
| 6 | 10.707 | Ala | 283665 | 6299060 | 4.886 | 435.301 |
| 7 | 12.153 | Val | 99883 | 1670980 | 1.293 | 151.446 |
| 8 | 16.920 | Leu | 47741 | 1782002 | 1.277 | 167.602 |
| 9 | 22.227 | NH3 | 39095 | 1153415 | 1.573 | 26.742 |
| 10 | 27.893 | Arg | 53613 | 1695540 | 1.273 | 221.792 |
| Totals | | | 1110727 | 23888201 | 18.253 | |

VIS 2 Results

| Pk# | RT | Name | Height | Area | ESTD Conc/nmol | Calc% |
|---|---|---|---|---|---|---|
| 1 | 7.660 | Pro | 49619 | 705304 | 2.501 | 287.839 |
| Totals | | | 49619 | 705304 | 2.501 | |

FIG. 1a Continued

Tumor cell apoptosis rate after SP2 administration (%)

Lymphocyte cd4+/cd8+ ratio after sp2 administration

SYNTHETIC PEPTIDE SP2 AND APPLICATION THEREOF

CROSS-REFERENCE TO RELATED APPLICATIONS

This application is a continuation of U.S. Utility application Ser. No. 17/056,414, filed Nov. 17, 2020, which is a U.S. national stage entry of PCT International Application No. PCT/CN2018/115567, filed Nov. 15, 2018, which claims the benefit to the priority of Chinese Patent Application No. 201811333589.1, filed Nov. 9, 2018, the content of which are incorporated herein by reference in their entireties.

INCORPORATION OF SEQUENCE LISTING

This application contains a sequence listing submitted in Computer Readable Form (CRF). The CFR file containing the sequence listing entitled "PA128-0088CON_ST25.txt", which was created on Jun. 28, 2022, and is 589 bytes in size. The information in the sequence listing is incorporated herein by reference in its entirety.

TECHNICAL FIELD

The present disclosure belongs to the technical field of biomedicine, and relates to a synthetic peptide sp2 and an application thereof, especially an application in preparing new non-cytotoxic anti-tumor drugs.

BACKGROUND

Cancer patients urgently need safe and effective anti-tumor drugs. Pancreatic cancer is extremely malignant and has an insidious onset. At first diagnosis, metastasis to peripancreatic organs or lymph nodes, liver metastasis, and distant metastasis have occurred. It is called the king of cancer. The most widely used in traditional chemotherapy for pancreatic cancer are cytotoxic anti-tumor drugs such as fluorouracil (5-FU), mitomycin (MMC), cisplatin (ADM), etc. Cytotoxic anti-tumor drugs have a strong killing or inhibitory effect on tumor cells, but for the treatment of pancreatic cancer, single-agent chemotherapy has poor efficacy and short survival, so combined chemotherapy is often used, such as FAM (5-FU, ADM, MMC), SMF (STZ, MMC, 5-FU) regimens, etc. Since taxol was launched, the TC (taxol+carboplatin) regimen has gradually become the first choice for the treatment of pancreatic cancer. Cervical cancer is the most common gynecological malignant tumor and the main disease that endangers women's health and life. Cervical cancer chemotherapy is mainly used for patients with advanced stage or recurrence and metastasis. Commonly used chemotherapy drugs include cisplatin, carboplatin, taxol, bleomycin, ifosfamide, fluorouracil and other cytotoxic anti-tumor drugs. While cytotoxic anti-tumor drugs kill or inhibit tumor cells, they also have an impact on normal cells of the body, especially cells with vigorous metabolism, and usually lead to adverse reactions in patients at effective doses. The positive control drug taxol used in the present disclosure belongs to a broad-spectrum cytotoxic anti-tumor drug, and is one of the most popular anti-cancer drugs in the international market in recent years. The American Cancer Institute predicts that paclitaxel is the most effective anti-cancer drug for humans in the next 20 years. However, toxic side effects such as allergic reactions, bone marrow suppression, neurotoxicity, and cardiovascular toxicity do more harm to cancer patients. Therefore, the preparation of new non-cytotoxic anti-tumor drugs has great social significance and strong market demand. So far, there is no similar non-cytotoxic anti-tumor synthetic peptide in the prior art. sp2 is a polypeptide composed of 8 kinds of amino acids, and its chemical synthesis, purification and structural confirmation all benefit from the achievements of biotechnology and an application thereof in biomedical technology. However, the research on the application of sp2 in new anti-tumor drugs is blank. The application of sp2 in the preparation of new anti-tumor drugs, including the safety and effectiveness of the anti-tumor effect of sp2 and various pharmacological and pharmacological activities thereof, is an original discovery.

SUMMARY OF THE INVENTION

The present disclosure adopts the solid-phase chemical synthesis technology to obtain the chemically synthesized synthetic peptide sp2 with a purity greater than 99% (FIGS. 1a-1c), having an amino acid sequence as shown in SEQ ID NO: 1, which is RVLNGPEEEAAAPAE; i.e., Arg Val Leu Asn Gly Pro Glu Glu Glu Ala Ala Ala Pro Ala Glu.

Compared to natural anti-tumor peptides, chemical synthesis can obtain high-purity polypeptide monomers. An application of the chemically synthesized peptide sp2 in preparing new non-cytotoxic anti-tumor drugs is disclosed.

The present disclosure also protects the application of the synthetic peptide 2 in any one of the following (1) to (8): (1) preventing and/or treating of tumor; (2) inhibiting proliferation and/or growth and/or invasion of tumor cells; (3) enhancing anti-tumor immune response; (4) inducing tumor cell differentiation; (5) preparing anti-tumor drug of class 1; (6) inhibiting tumor telomerase activity; (7) regulating tumor cell cycle; (8) preparing a class of product for regulating the tumor cell cycle.

The present disclosure adopts the solid-phase chemical synthesis technology to obtain the chemically synthesized synthetic peptide sp2 with purity greater than 99% (FIGS. 1a-1c), and an application of the chemically synthesized synthetic peptide sp2 in preparing new non-cytotoxic anti-tumor drugs is disclosed.

Further, the application of the above-mentioned synthetic peptide sp2, the tumor in any one of (1) to (8) comprises human pancreatic cancer in situ, human cervical cancer, human ovarian cancer, human osteosarcoma, human lung adenocarcinoma and human poorly differentiated pregastric cancer.

Further, the above-mentioned tumor cells specifically listed in the examples are human pancreatic cancer in situ BxPC-3, human cervical cancer SiHa, human ovarian cancer A2780, human osteosarcoma MG-63, human lung adenocarcinoma A549 and human poorly differentiated pregastric cancer BGC-823 respectively.

The anti-tumor effect of sp2 has both safety and effectiveness; wherein, the safety includes the verification results of the upper and lower methods and the maximum dose method used in the examples, and specifically the maximum non-toxic dose of sp2 administered intravenously is tested. After injecting sp2 at a dose of 2000 mg/kgBW into the tail vein of Kunming mice, they are continuously observed for 14 days within a specified time, and there is no toxicity or death, and no abnormality after general dissection. Conclusion: the maximum non-toxic dose of sp2 administered intravenously is 2000 mg/kgBW.

The effectiveness includes the effectiveness verification results of the anti-tumor efficacy on human pancreatic cancer, human cervical cancer, human ovarian cancer, human osteosarcoma subcutaneously in nude mice in the examples, as well as the effect results on in situ transplantation human pancreatic cancer and human lung adenocarcinoma subcutaneously in nude mice in delaying tumor metastasis and prolonging the median survival time of tumor-bearing nude mice, which has no significant difference in efficacy intensity compared with the positive control taxol group.

Synthetic peptide sp2 is a multi-functional biologically-active molecule that participates in multiple functional activities at the same time: a. inhibiting telomerase activity. Telomerase can catalyze the replication of telomere DNA. Telomere is located at the end of chromosome and consists of a repetitive sequence TTAGGG and a telomere binding protein. Telomere DNA plays an important role in maintaining cell division. Every time a human cell divides, the telomere is shortened once. When the telomere is shortened to a certain degree, the cell can no longer divide, but once the cell becomes cancerous, it divides and proliferates indefinitely. Telomerase is a ribonucleoprotein enzyme complex, which is a special reverse transcriptase, being composed of RNA and protein. The RNA component is the template of telomere sequence. Telomerase synthesizes telomere DNA fragments through its own RNA template. Tumor telomerase activity is likely to be one of the important reasons for tumor malignant hyperplasia; b. inducing malignant tumor cell differentiation. After the cell becomes cancerous, the phenotype of the tumor cell returns to an undifferentiated state, and abnormal differentiation appears. Cell proliferation to differentiation is a process of cell cycle arrest and activation to induce differentiation (changes in cell morphology and function); c. enhancing T cell transformation, and T lymphocytes play a vital role in the body's anti-tumor process; d. enhancing the immune effect of removing tumor cells: tumor cells can produce immune tolerance by inhibiting the effective recognition and killing of tumor cells by the immune system. CD47 and PD-L1 are highly expressed on the surface of tumor cells and bind to the corresponding antigens on the surface of macrophages and T lymphocytes respectively, thereby making immunity function is inhibited.

The present disclosure also protects a biologically-active molecular product of which the active ingredient is synthetic peptide sp2; since the anti-tumor effect of sp2 has a clear target, it can be used as a single medication, and synthetic peptide sp2 is used as the only effective active ingredient of the biologically-active molecular product, and the experiment proves that the curative effect is significant.

Beneficial Effects

The present disclosure has found in the in vitro screening test that sp2 has obvious proliferation inhibitory activity on human pancreatic cancer BxPC-3 (FIG. 2).

The in vivo efficacy test of sp2 uses nude mouse subcutaneous and nude mouse human carcinoma in situ xenograft tumor models. The evaluation indexes of the anti-tumor activity effectiveness of sp2 on human cancer xenograft tumor model subcutaneously in nude mice include two in vivo efficacy evaluation indexes: relative tumor proliferation rate T/C (%) and tumor growth inhibition rate (%). It has obvious efficacy on human cervical cancer SiHa, human pancreatic cancer in situ BxPC-3, human ovarian cancer A2780, human osteosarcoma MG-63 and human poorly differentiated pregastric cancer BGC-823 subcutaneously in nude mice, and has a significant dose-effect and time-effect relationship (FIGS. 3a-3e).

Tumor metastasis and recurrence are important reasons for the death of tumor patients. The sp2 of the present disclosure can significantly delay the occurrence of tumor metastasis of the xenograft tumors of nude mouse human lung adenocarcinoma in situ A549 and human pancreatic cancer in situ BxPC-3, and prolong the median survival time of tumor-bearing nude mice (FIGS. 4a and 4b). In vivo imaging shows that there is no difference between the fluorescence intensity of the sp2 high-dose group and the positive control taxol group, that is, there is no difference in efficacy of the two groups (FIG. 5).

The safety of sp2 lies in that after the upper and lower methods of acute toxicity test and the maximum dose method are used to inject sp2 at a dose of 2000 mg/kgBW into the tail vein of ICR and Kunming mice respectively, no damage is found within a specified time (continuous Observation for 14 days), including no obvious behavioral abnormalities, no weight loss, and no death. After the experiment, no tissue or organ abnormality is found after general dissection. It is proved that the maximum non-toxic dose of intravenous administration is 2000 mg/kgBW (Examples 12, 13 and FIG. 12).

The immortal division and proliferation of tumor cells are related to the continuous synthesis of telomere DNA fragment TTAGGG by telomerase through its own RNA template. sp2 can significantly inhibit tumor telomerase activity (FIG. 6);

It is found in the application that sp2 has an obvious inducing differentiation effect on malignant tumor cell HL-60 and its inducing differentiation process is (FIGS. 7a-7c): after sp2 is incubated with acute promyelocytic leukemia cell HL-60 for 5 days, the HL-60 cell cycle is detected by flow cytometry. Compared with the control group, after sp2 treatment, the expression of cells in the HL-60G0/G1 phase is increased significantly, the expression of cells in the G2/M phase is reduced, and the expression of cells in the S phase is reduced, showing a G1 phase arrest (FIG. 7a); At the same time, after sp2 is incubated with acute promyelocytic leukemia cell HL-60 for 5 days, mature cells are increased significantly (FIG. 7b) in the tumor cell HL-60 morphology, and the NBT reduction ability is significantly enhanced (FIG. 7c) in the function, indicating that cell proliferation to differentiation is a process of cell cycle arrest and activation to induce differentiation (morphological and functional changes), and sp2 has a significant role in promoting differentiation of tumor cells.

The present disclosure has found that when sp2 is administered in vivo at 16 mg/kg/day for 4 consecutive weeks, subcutaneous human xenograft tumors in nude mice (the tumor cells of osteosarcoma, ovarian cancer and human poorly differentiated pregastric cancer tested) show obvious apoptosis (FIG. 8).

Tumor metastasis is related to the immune regulation of the body's elimination of tumor cells. And T lymphocytes play a vital role in the body's anti-tumor process. Using flow cytometry, it is found that in the positive control group taxol significantly reduces the content of T lymphocytes in peripheral blood (p<0.05), while sp2 has a tendency to increase the content of T cells, which is significantly different from the taxol group (P<0.05) (FIG. 9).

The spleen is taken to prepare a spleen cell suspension, and stimulated with ConA-mitogen. The OD value is measured by MTT to reflect the proliferation of cells. It is found that sp2 significantly enhances the proliferation activity of T lymphocytes in tumor-bearing nude mice (MG-63), and has obvious dose-response relationship, while the positive control taxol group significantly inhibits the proliferation of T lymphocytes induced by ConA-mitogen stimulation (FIG. 10).

Tumor cells can produce immune tolerance by inhibiting the effective recognition and killing of tumor cells by the immune system. CD47 and PD-L1 are highly expressed on the surface of tumor cells and bind to the corresponding antigens on the surface of macrophages and T lymphocytes respectively, thereby making immunity function is inhibited. sp2 can obviously inhibit the high expression of CD47 and PD-L1 in tumor cells, and enhance the immune effect of clearing tumor cells (FIGS. 11a and 11b).

BRIEF DESCRIPTION OF DRAWINGS

FIGS. 1a, 1b and 1c. Amino acid composition, chromatographic and mass spectrometry analysis of sp2, in which: FIG. 1a is the amino acid composition analysis; FIG. 1b is chromatography (RP-HPLC) purification; FIG. 1c is mass spectrometry analysis ESI-MS;

FIG. 3b. illustrates the effect of sp2 on the relative tumor proliferation rate T/C (%) of human cervical cancer SiHa xenograft tumor subcutaneously in nude mice;

FIG. 3c. illustrates the effect of sp2 on the tumor weight of human cervical cancer SiHa xenograft tumor subcutaneously in nude mice;

FIG. 3d. is the photos of tumor-bearing nude mice in each group: from top to bottom, they are model group, sp2 low dose group, sp2 medium dose group, and sp2 high dose group;

FIG. 3e. is the tumor photos of tumor-bearing nude mice in each group;

FIG. 4b. The effect of sp2 on survival time of human lung adenocarcinoma in situ A549 tumor-bearing nude mice;

Figure 1A:
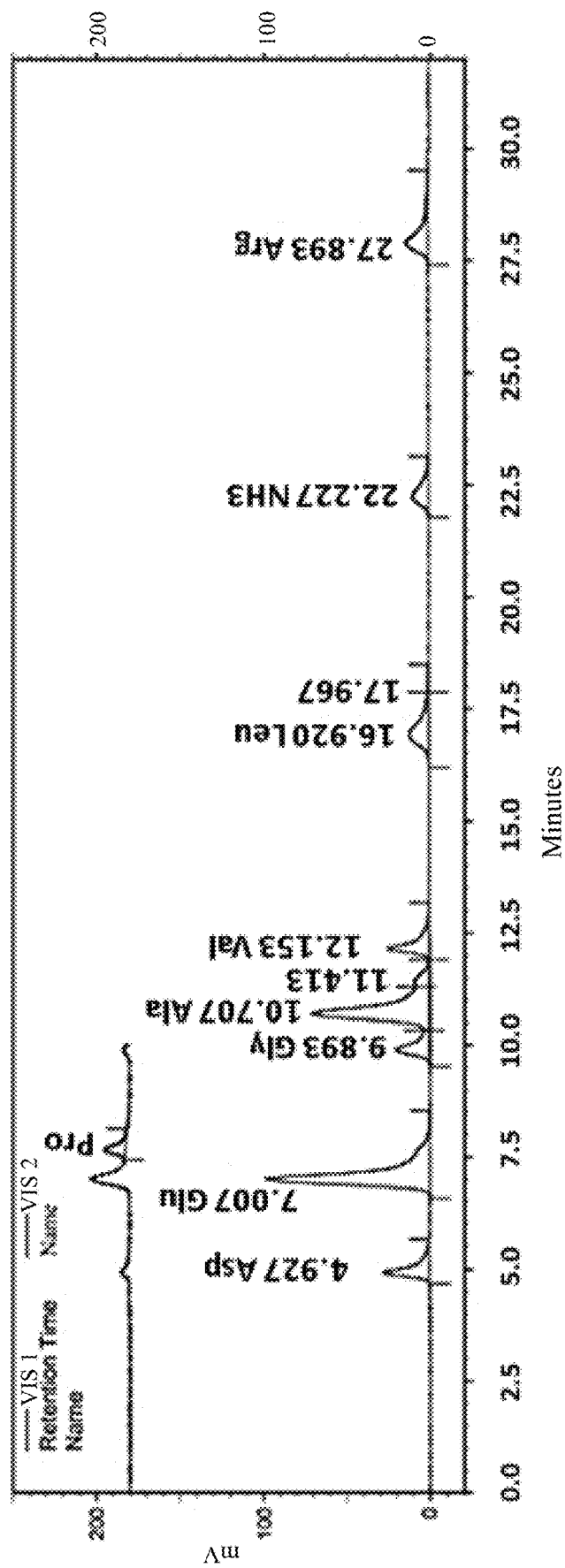
Figure 1B:
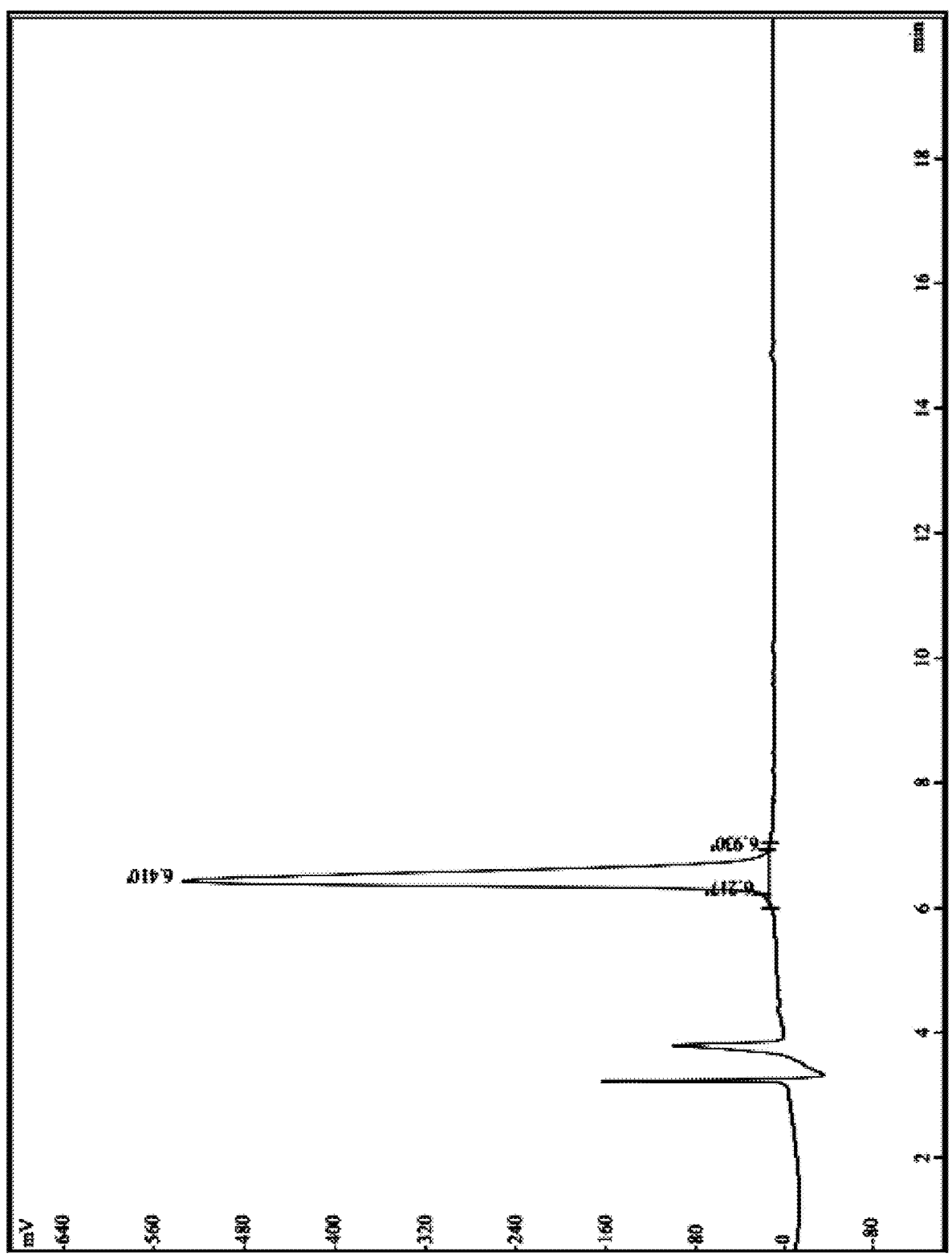
Figure 1C:
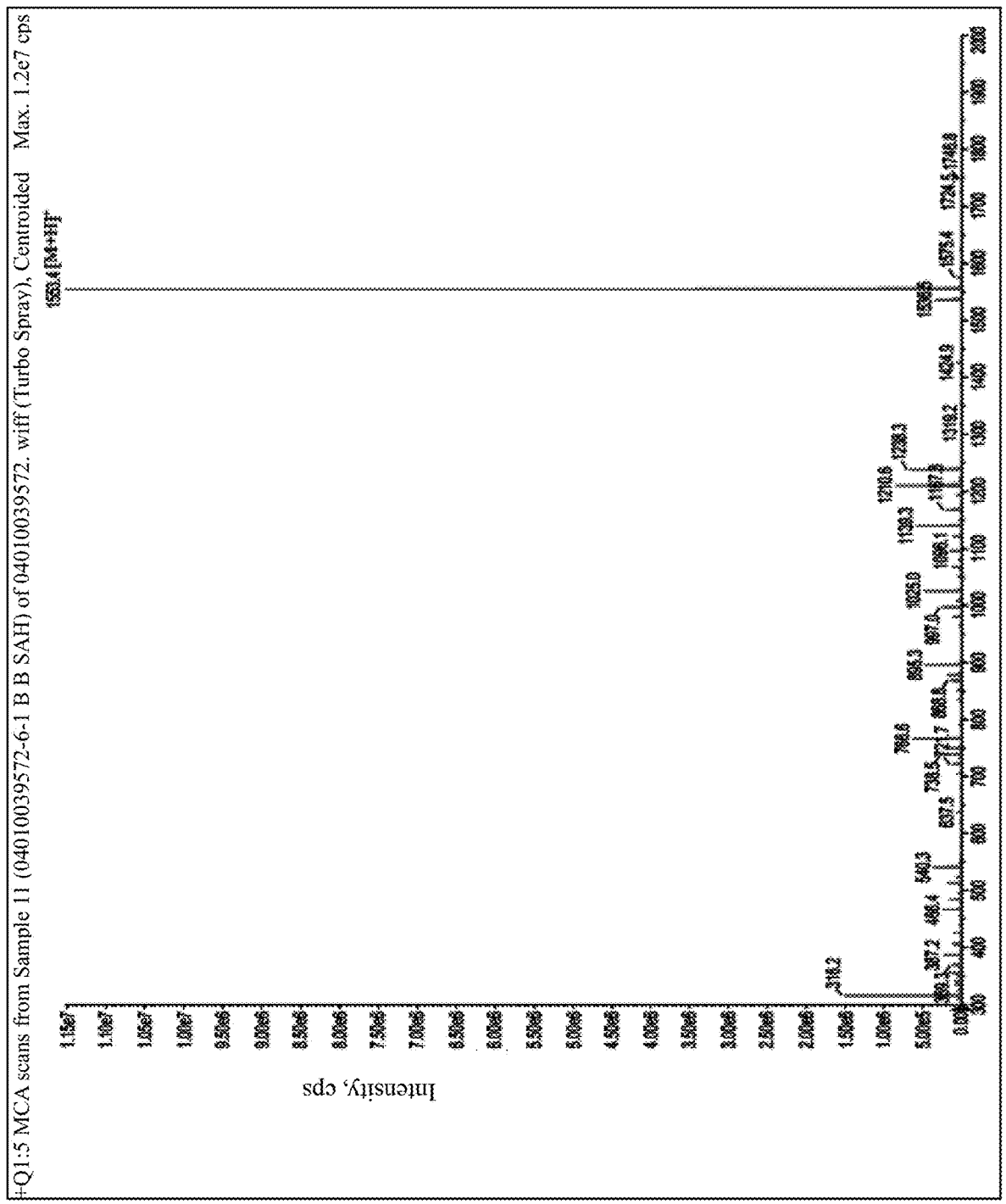
Figure 5:
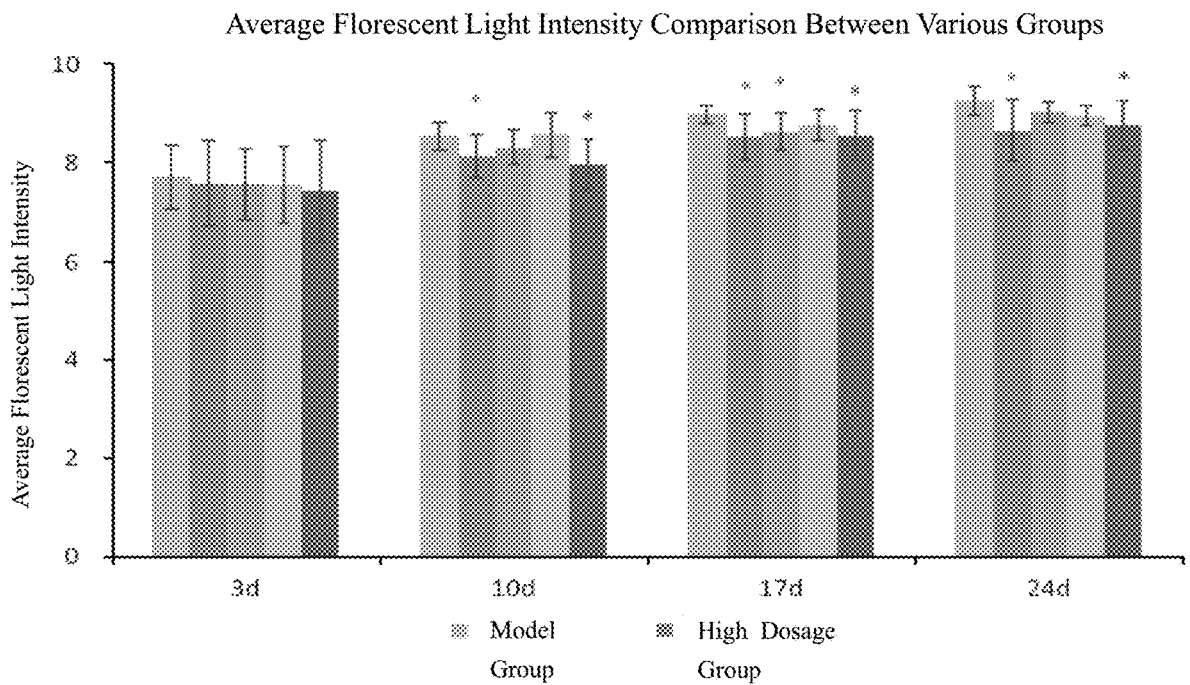
Figure 6:
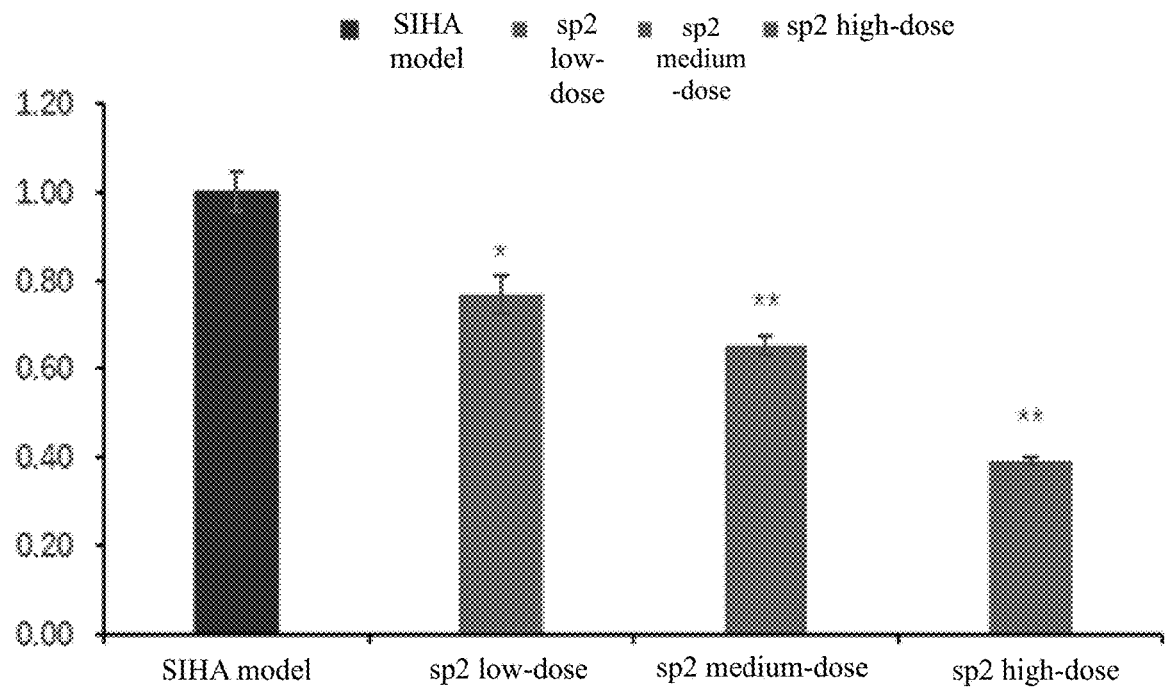
Figure 7A:
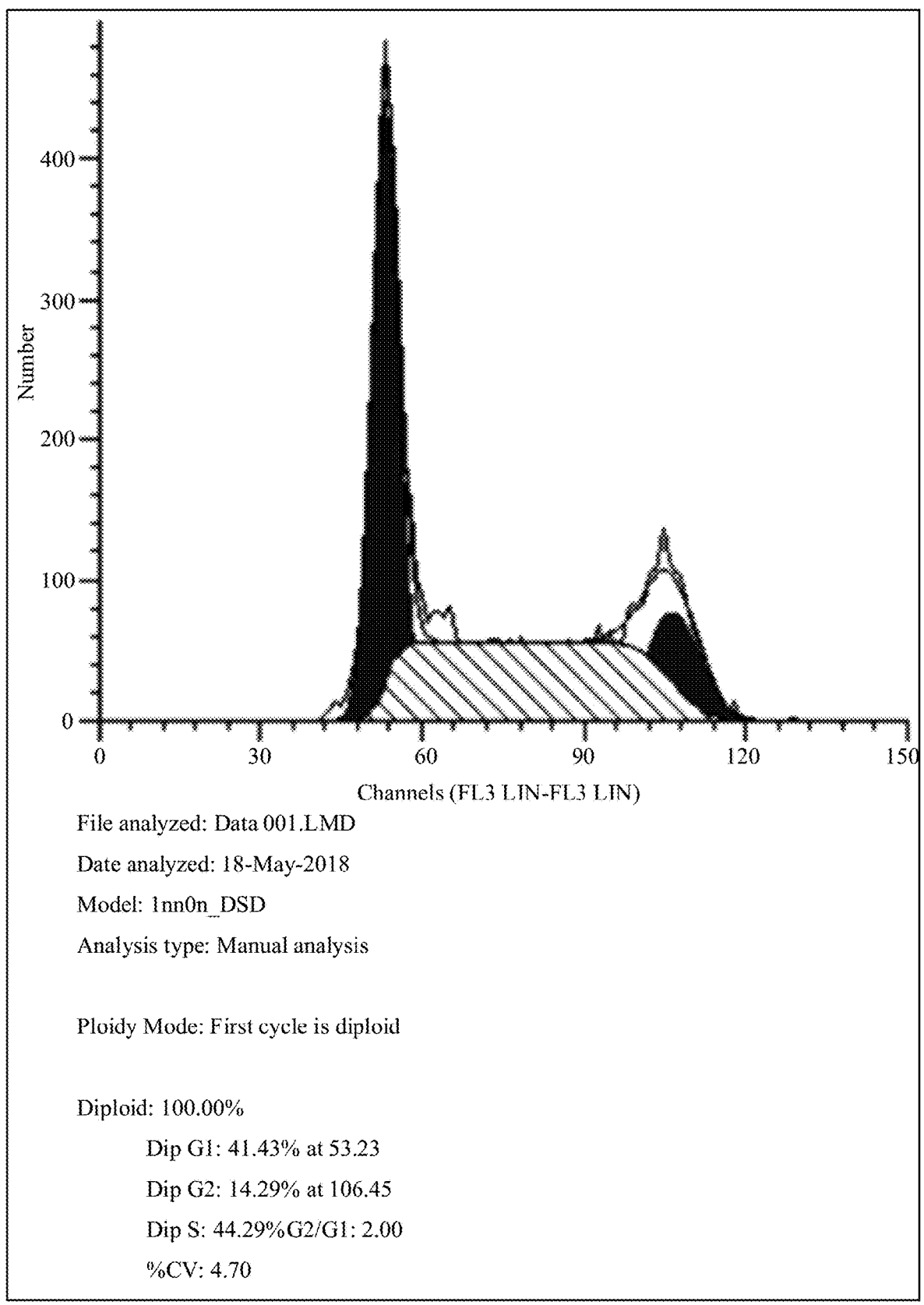
Figure 7A:
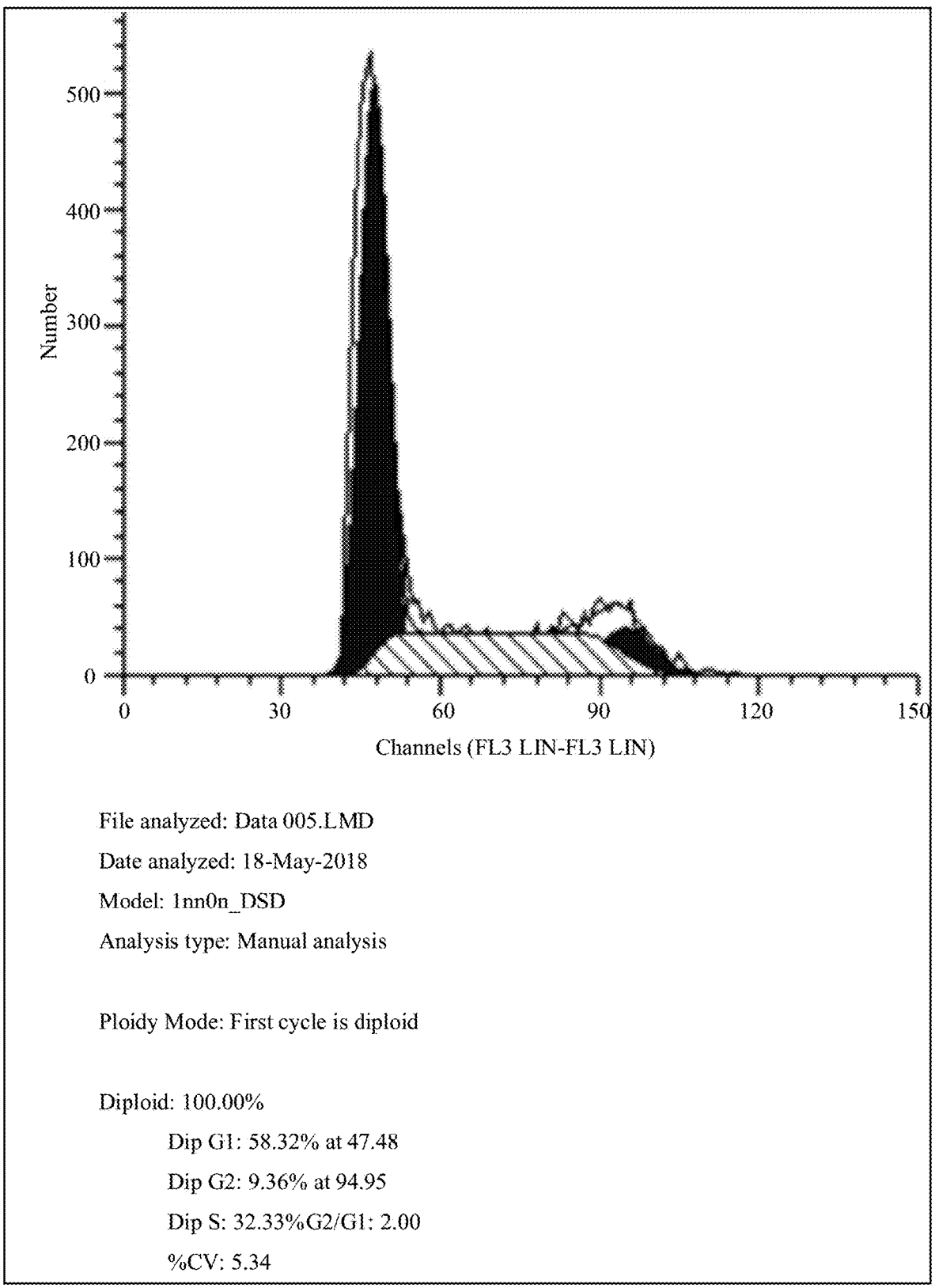
Figure 7A:
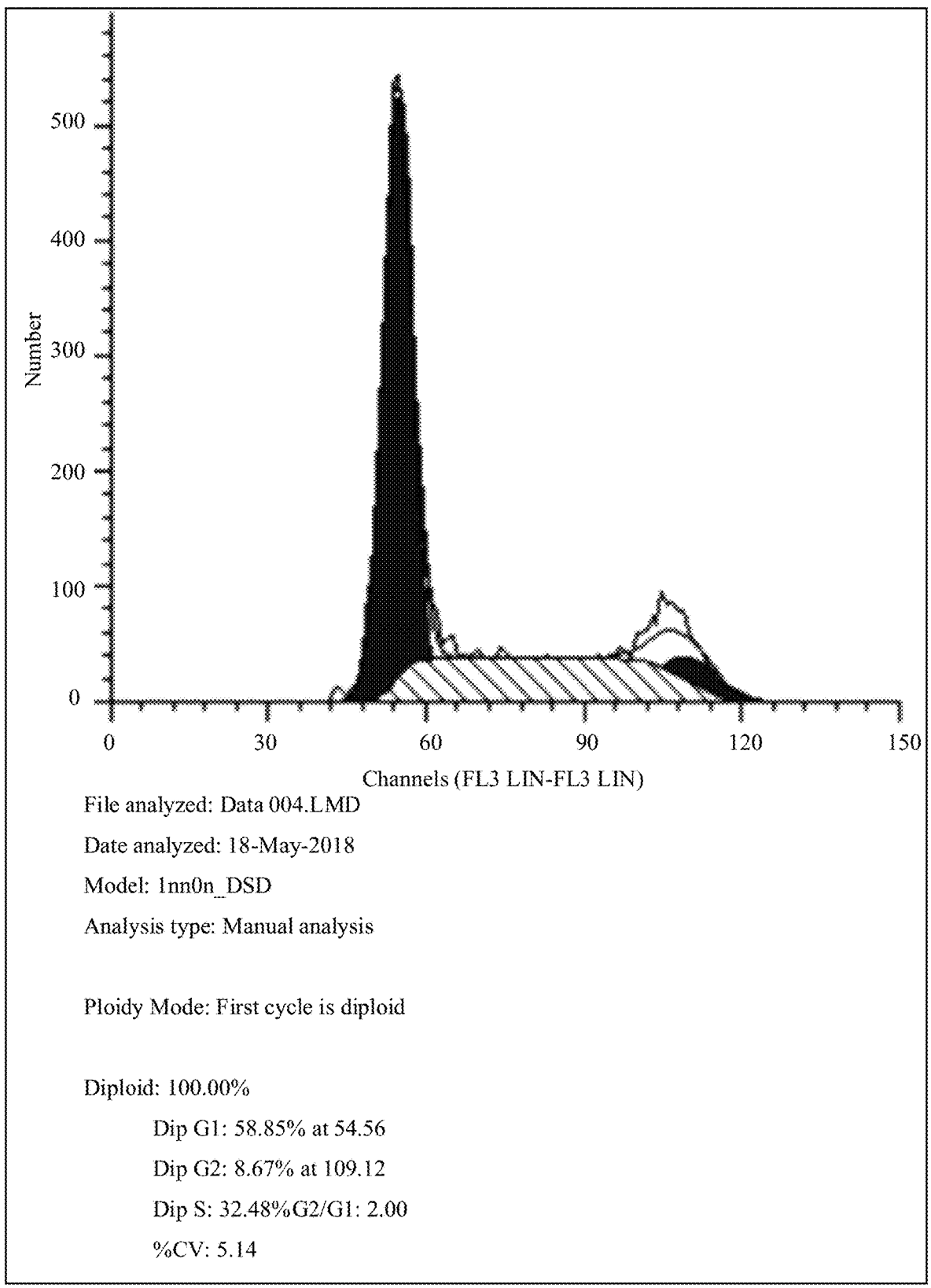
Figure 7A:
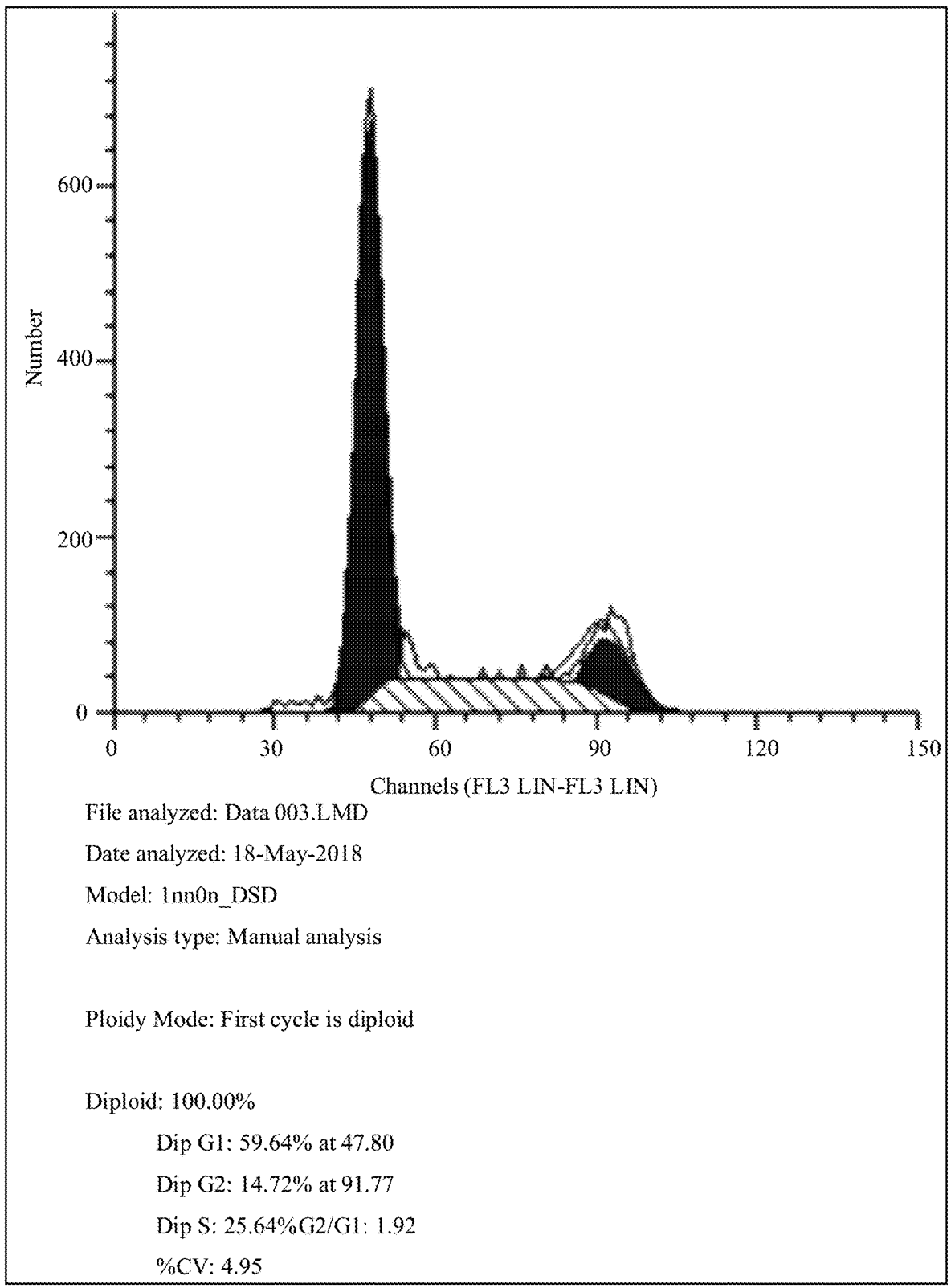
Figure 7A:
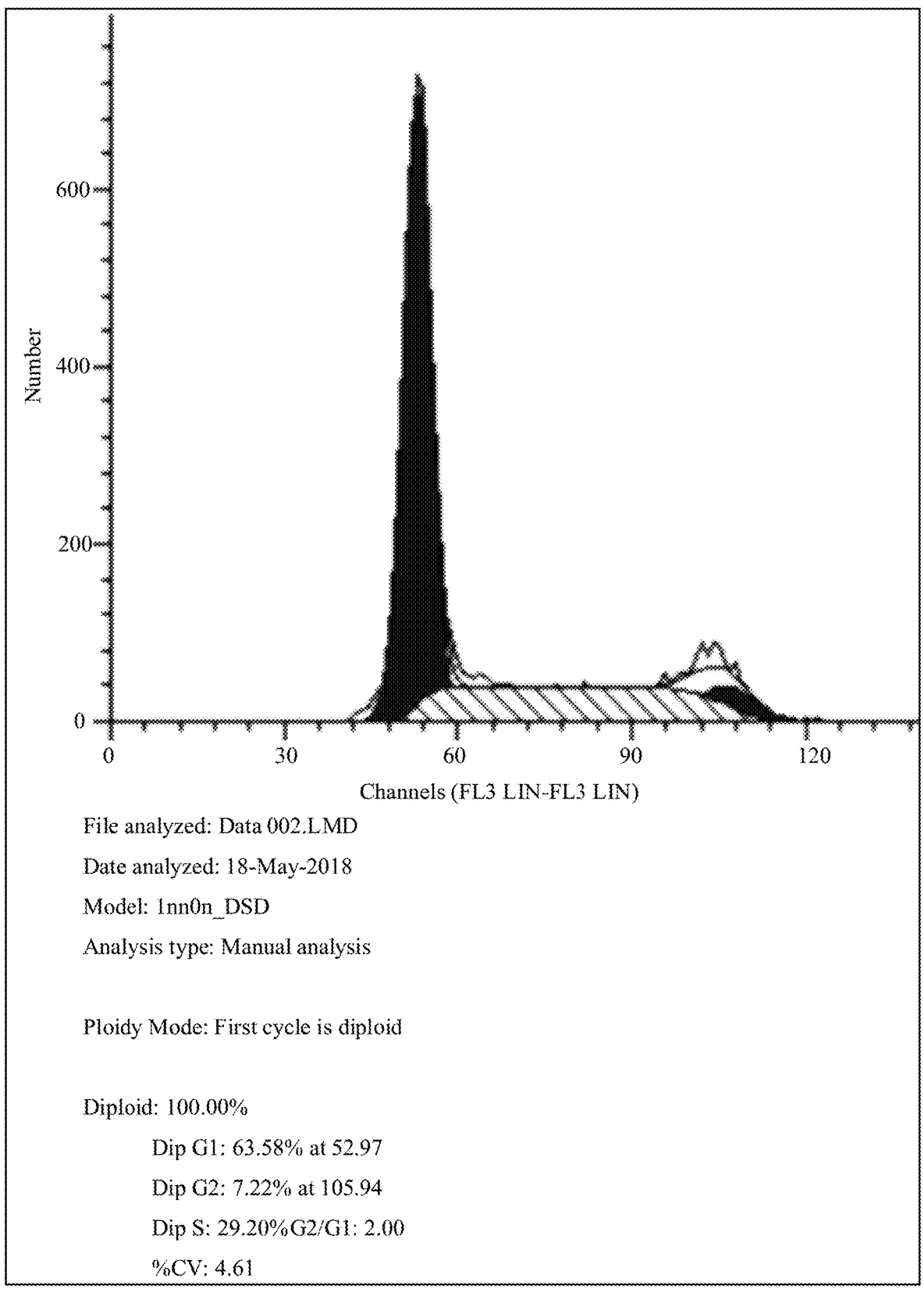
Figure 7B:
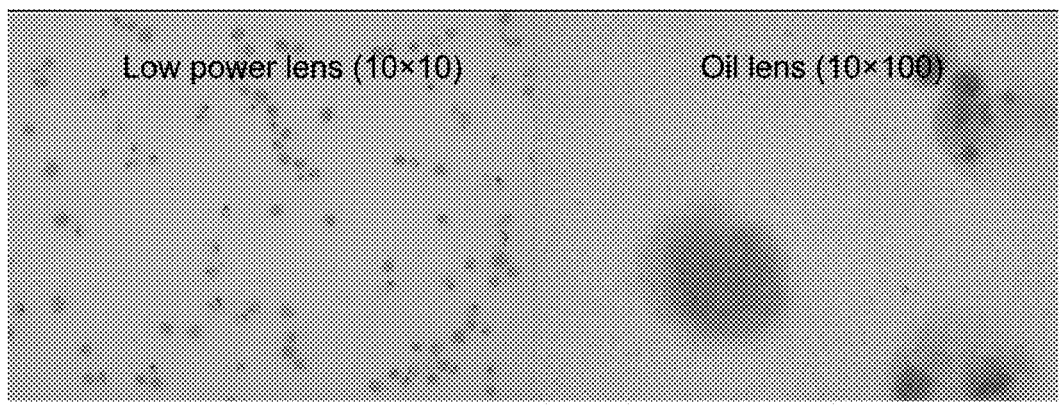
Figure 7B:
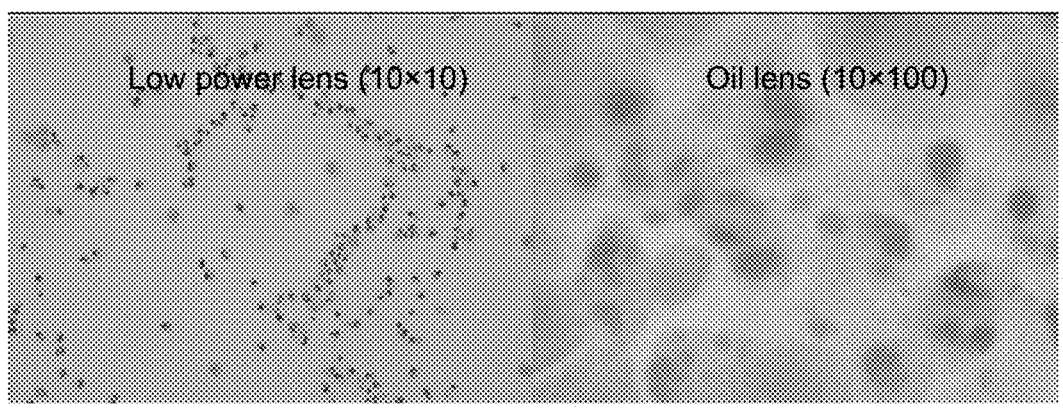
Figure 7C:
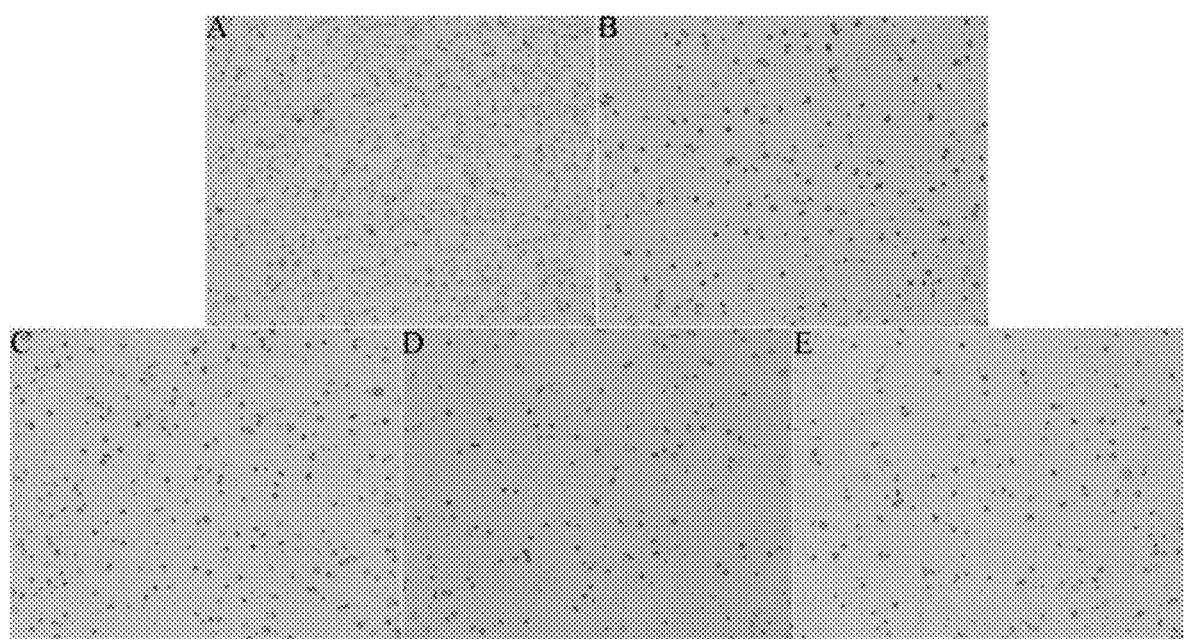
Figure 8:
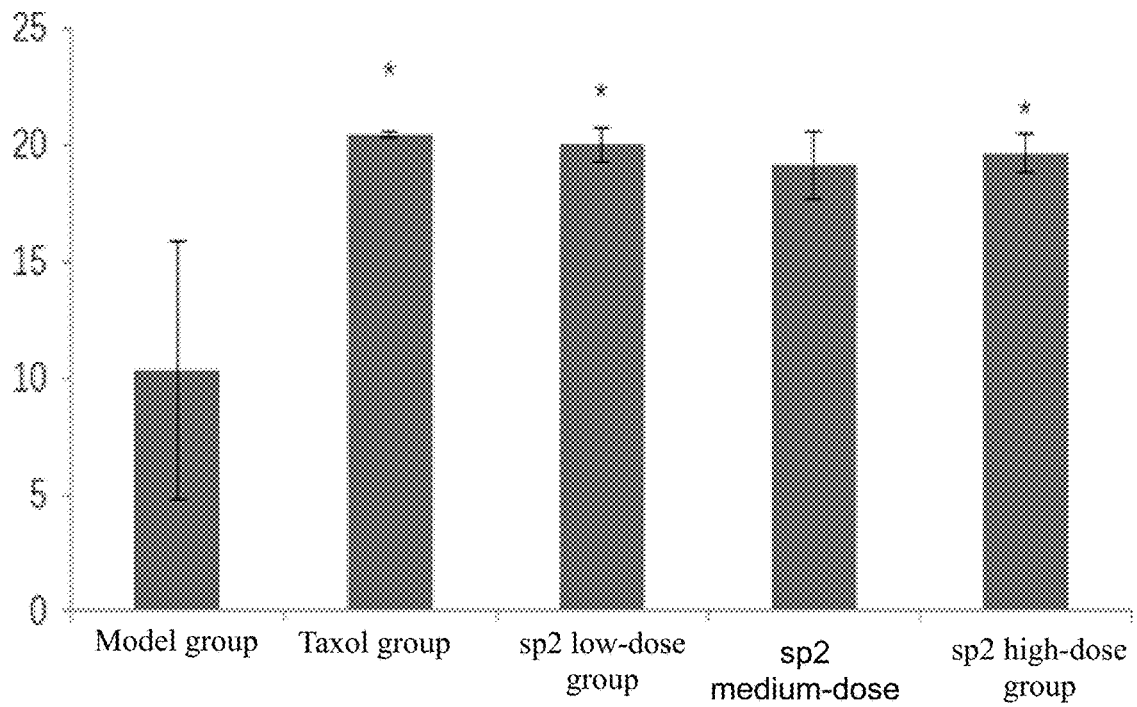
Figure 9:
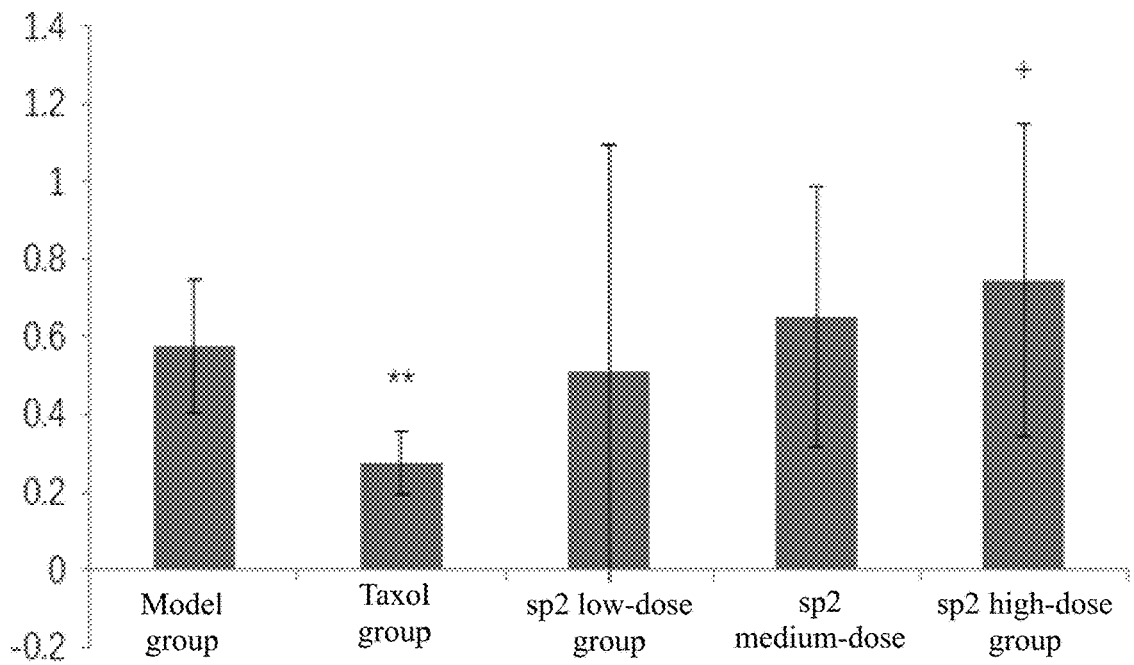
Figure 10:
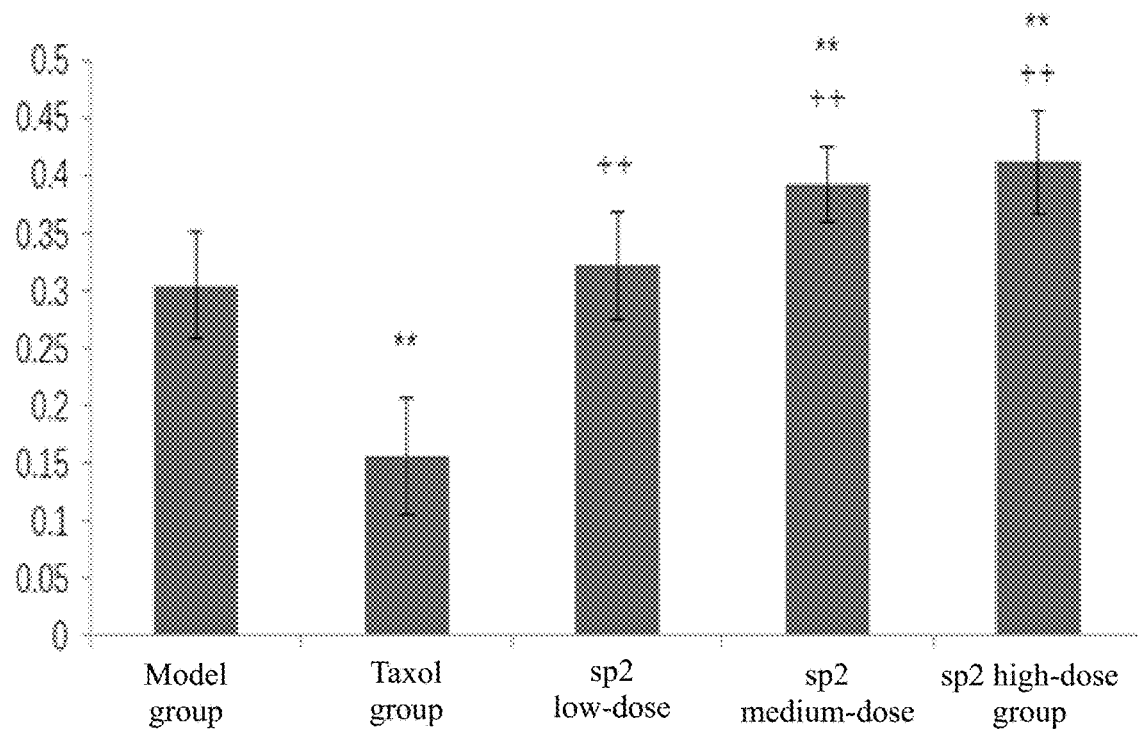
Figure 11A:
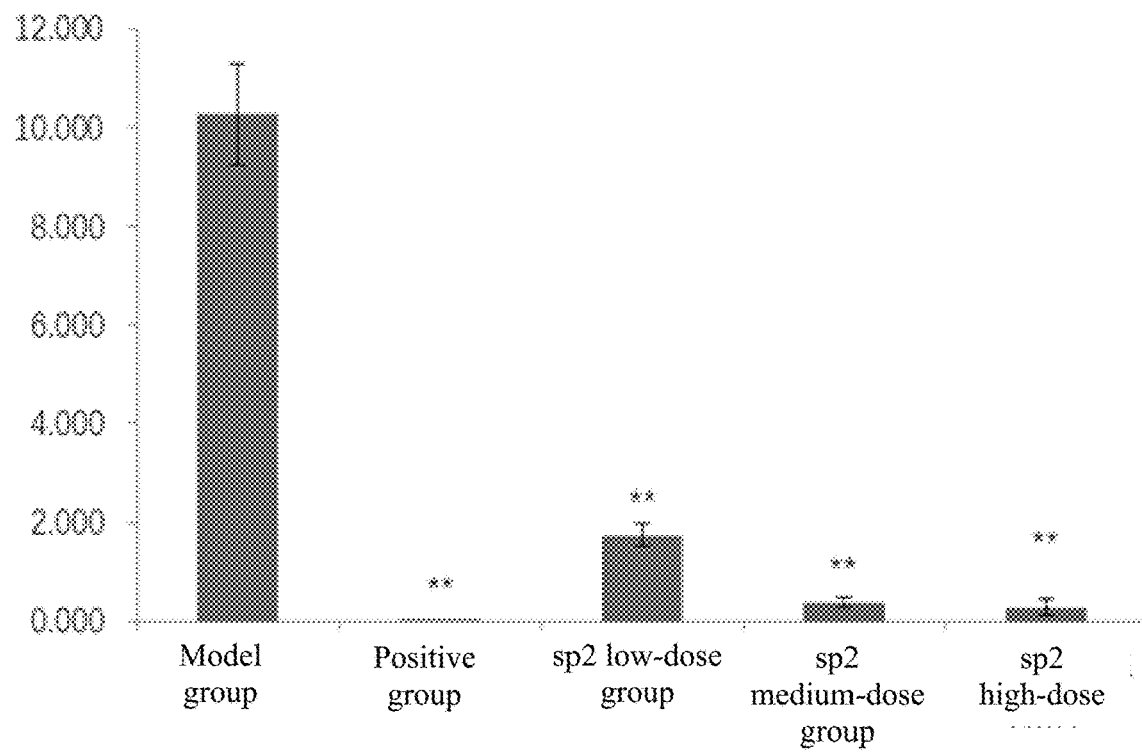
Figure 11B:
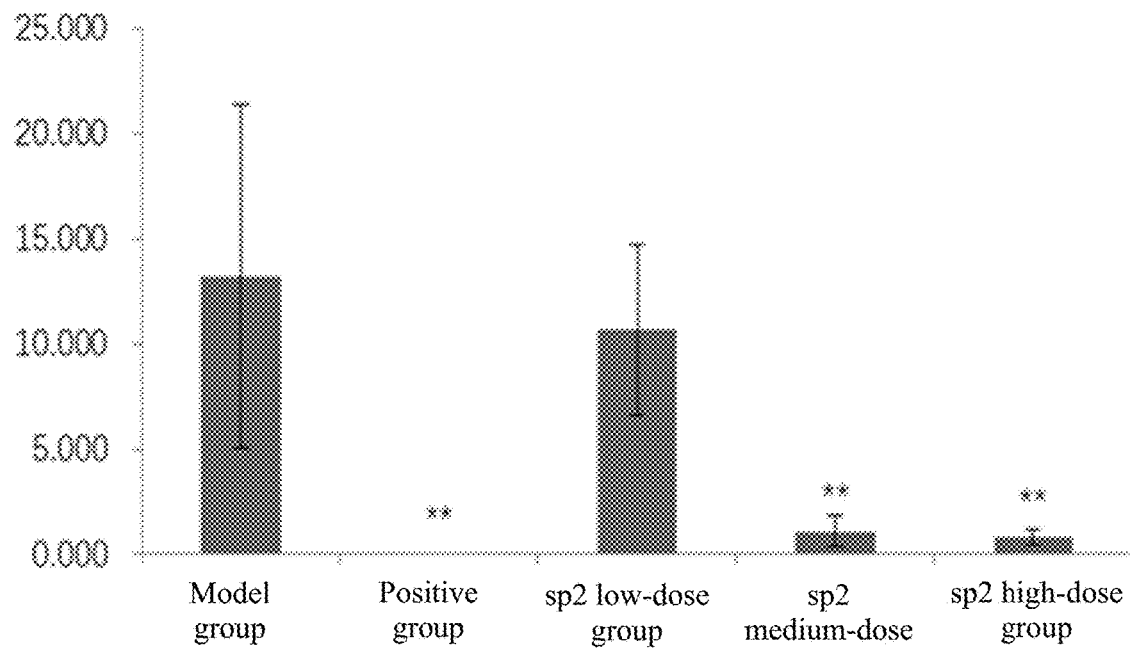
Figure 12:
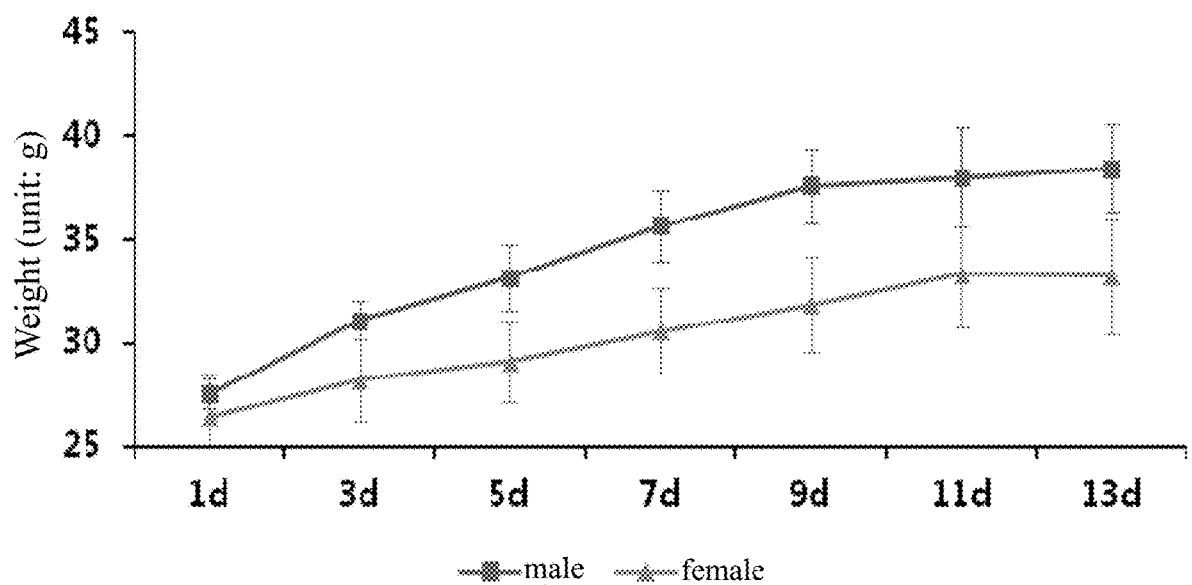

5 d model group: on day 5, tumor fluorescence is mainly concentrated in the lungs, and no extrapulmonary metastasis is found;

5 d high-dose administration group: on day 5, tumor fluorescence is mainly concentrated in the lungs, and no extrapulmonary metastasis is found;

12 d model group: on day 12, 8 nude mice have tumor extrapulmonary metastasis, and the other 2 nude mice have no tumor metastasis;

12 d high-dose administration group: on day 12, tumor fluorescence was still concentrated in the lungs, and no extrapulmonary metastasis was seen;

19 d model group: on day 19, 2 nude mice die, 8 surviving mice have extensive metastasis, and the fluorescence signal is very strong;

19 d high-dose administration group: on day 19, no death occurs and no extrapulmonary metastasis is seen in 2 nude mice, and extrapulmonary metastasis is seen in the other 8 nude mice;

FIG. 5. In vivo efficacy of sp2 on the xenograft tumor of human pancreatic cancer in situ BxPC-3 subcutaneously in nude mice, and in vivo imaging fluorescence intensity shows that compared with the model group, * means significant difference (P<0.05); and there is no difference between the efficacy fluorescence intensity of the sp2 high-dose group and the positive control taxol group (P>0.05);

FIG. 6. Sp2 inhibits tumor telomerase activity; the effect of sp2 on telomerase activity of human cervical cancer SiHa xenograft tumor subcutaneously in nude mice; sp2 significantly inhibits telomerase activity of human cervical cancer SiHa xenograft tumor subcutaneously in nude mice, and compared with the model group, a low concentration of sp2 can reduce telomerase activity (P<0.05), and a medium-high concentration can significantly reduce telomerase activity (P<0.01);

FIGS. 7a, 7b and 7c. sp2 has an obvious inducing differentiation effect on malignant tumor cell HL-60; sp2 induces the transformation of HL-60 cell line of human acute granulocytic leukemia into normal granulocytes, wherein:

FIG. 7a. FCN detection: the effect of different doses of sp2 on the cell cycle of HL-60; A. control group, B. 25 μM, C 50 μM, D.100 μM, E.200 μM;

FIG. 7b. the effect of sp2 synthetic peptide on the cell morphology of HL-60; top: control group, bottom: 200 μM;

FIG. 7c. the effect of different doses of sp2 synthetic peptide on the in vitro inducing differentiation effect of HL-60 (NBT reduction reaction); A. control group, B.25 μM, C.50 μM, D.100 μM, E.200 μM;

FIG. 8. sp2 induces nude mouse tumor cell apoptosis; sp2 promotes obvious apoptosis of transplanted tumor cells of human osteosarcoma MG63 subcutaneously in nude mice; compared to the model group, the taxol group can increase tumor cell apoptosis rate (P<0.05); compared to the model group, sp2 also has a significant pro-apoptotic effect;

FIG. 9. flow cytometry is used to detect the content of peripheral blood T lymphocytes; wherein, * indicates that there is a difference compared to the model group (P value<0.05); ** indicates that there is a significant difference compared to the model group (P value<0.01); + means that there is a difference compared with the positive control taxol group (P value<0.05); ++ means that there is a significant difference compared to the positive control taxol group (P value<0.01);

The positive control taxol group shows obvious toxicity to T lymphocytes, compared to the model group, there is a significant difference (P<0.01);

As the dose of sp2 increases, there is a tendency to promote the increase of T lymphocytes, but there is no significant difference compared to the model group (P>0.05); compared to the positive control taxol group, the sp2 high-dose group can promote increase of the content of T lymphocyte (P<0.05);

FIG. 10. Nude mouse splenic lymphocyte transformation experiment; the positive control taxol is significantly reduced, and sp2 significantly enhances the proliferation effect of T lymphocytes; * indicates that there is a difference compared to the model group (P value<0.05); ** indicates that there is a significant difference compared to the model group (P value<0.01); + means that there is a difference compared with the positive control taxol group (P value<0.05); ++ means that there is a significant difference compared to the taxol group (P value<0.01);

Compared to the model group, the taxol group significantly reduces transformation efficiency of T lymphocytes (P<0.01);

Compared to the model group, sp2 significantly enhances the transformation efficiency of T lymphocytes and is dose-dependent, wherein there is no difference in the low-dose group (P>0.05), and there is significant difference in the medium-dose group and the high-dose group (P<0.01); compared to the positive control taxol group, each group can significantly improve the transformation efficiency of T lymphocytes after sp2 administration (P<0.01);

FIGS. 11a and 11b. It can significantly inhibit the high expression of CD47 and PD-L1 in tumor cells; sp2 significantly inhibits the high expression of PD-L1 and CD47 in tumor cells;

FIG. 11a. CD47 expression changes, the sp2 administration group is significantly lower than the model group, with a dose-effect relationship;

FIG. 11b. PD-L1 expression changes, the sp2 medium-dose group and high-dose group are significantly lower than the model group;

FIG. 12. Acute toxicity test (maximum dose method), the animal body weight change curve within two weeks after injecting 2000 mg/kgBW of sp2 into the tail vein of Kunming mice.

DETAILED DESCRIPTION OF PREFERRED EMBODIMENTS

The following non-limiting examples may enable those of ordinary skill in the art to more fully understand the present disclosure, but do not limit the present disclosure in any way.

Example 1

Amino Acid Composition, Solid-Phase Chemical Synthesis, Chromatographic Purification and Mass Spectrometry Identification 1) Analysis of the amino acid composition of sp2: 10.2 mg sample was weighed and was dissolved with 7 mL of 6N HCl, and hydrolyzed at 110° C. under nitrogen protection for 22 hours. The reaction solution was transferred to a 10 mL volumetric flask after cooling, and was made to volume. 0.2 mL of the solution was taken and blown dry with nitrogen at 55° C.; 1 mL of distilled water was added and dried, and repeated three times. The dried product was dissolved thoroughly with 1.2 mL of deionized water (pH was adjusted with 0.02 mol/L HCl) and mixed well. It was filtered with 0.45 μM filter membrane, and injected 20 μL for computer testing (Hitachi L-8900 amino acid analyzer).

2) Solid-phase chemical synthesis, purity detection and molecular weight confirmation of sp2:

The solid-phase chemical synthesis of sp2 used the polypeptide Fmoc solid-phase synthesis technology, which was a process of repeatedly adding amino acids, from the C-terminus to the N-terminus of the known polypeptide amino acid sequence. First, the carboxyl group of the first amino acid at the C-terminus of the target polypeptide was covalently linked to the solid phase carrier (resin), and then the amino group of the amino acid was used as a starting point for synthesis to undergo acylation with the carboxyl group of the adjacent amino acid to form a peptide bond. The process was repeated until the target peptide was synthesized and then the target polypeptide was cut from the resin while removing the side chain protecting group. Finally, ice ether was added to precipitate the crude peptide;

3) High performance liquid chromatography was used for separation and purification: RP-HPLC 4) Mass spectrometry was used for purity detection and molecular weight confirmation (FIGS. 1a, b, c).

Example 2

Cell Proliferation Inhibition Test

Figure 2:
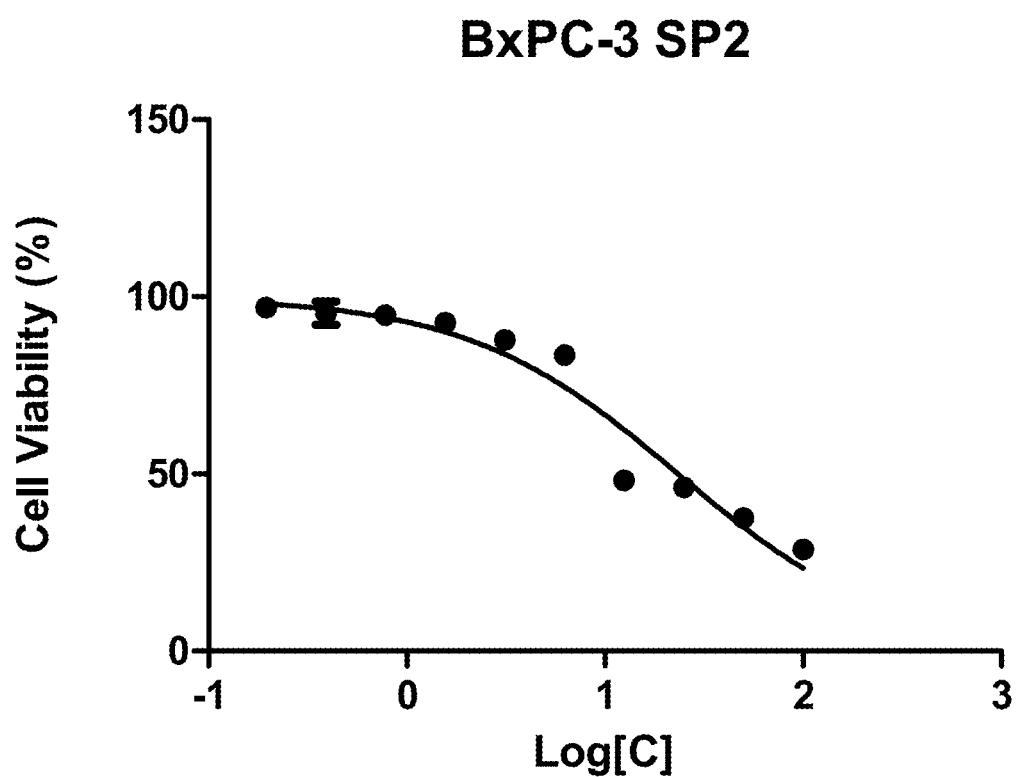
FIG. 2. In vitro pharmacodynamic activity screening test of sp2 (CCK method): using 22 cell lines of human cancer added with different concentrations of sp2 and incubated together for 72 hours, the CCK method is used for detection. Positive and negative control groups, 5 duplicate tubes, and 10 concentration gradients are set in the test, and the $IC_{50}$ value of sp2 is calculated. Inhibition rate and $IC_{50}$ value of sp2 on the in vitro proliferation activity of in situ human pancreatic cancer cell BxPC-3(%).
Figure 3A:
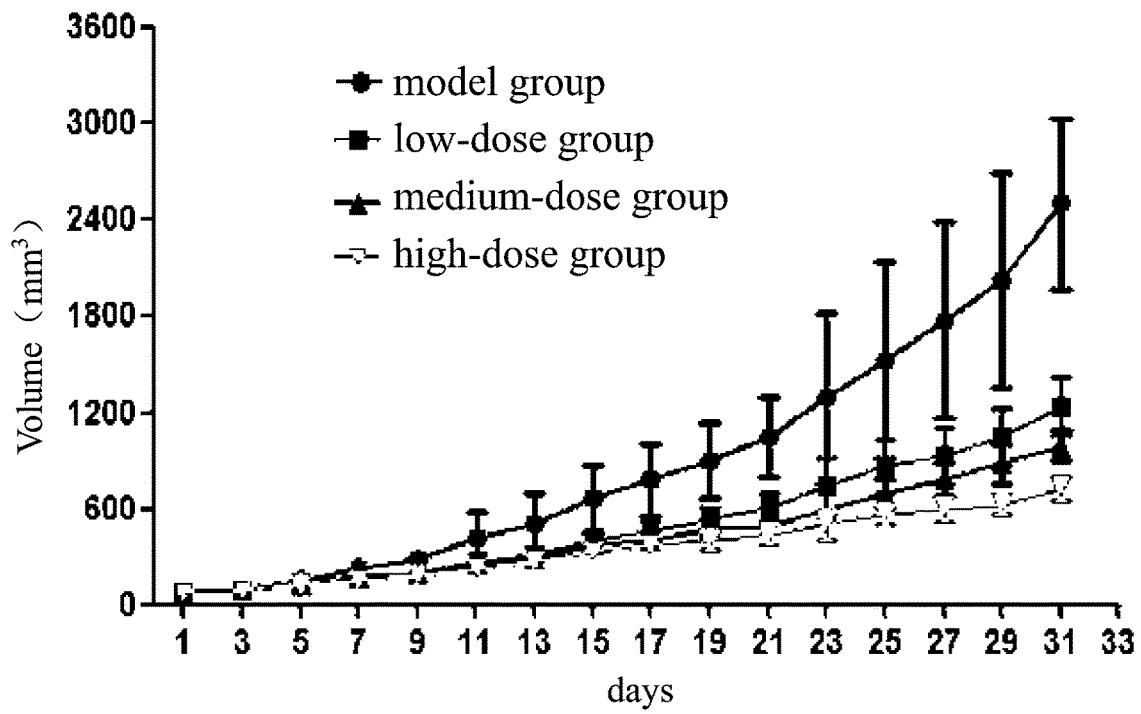
FIGS. 3a, 3b, 3c, 3d, and 3e. In vivo efficacy of sp2 on nude mouse subcutaneous xenograft tumors such as human cervical cancer SiHa, wherein, FIG. 3a. illustrates the effect of sp2 on the growth volume of human cervical cancer xenograft tumors subcutaneously in nude mice.
Figure 3B:
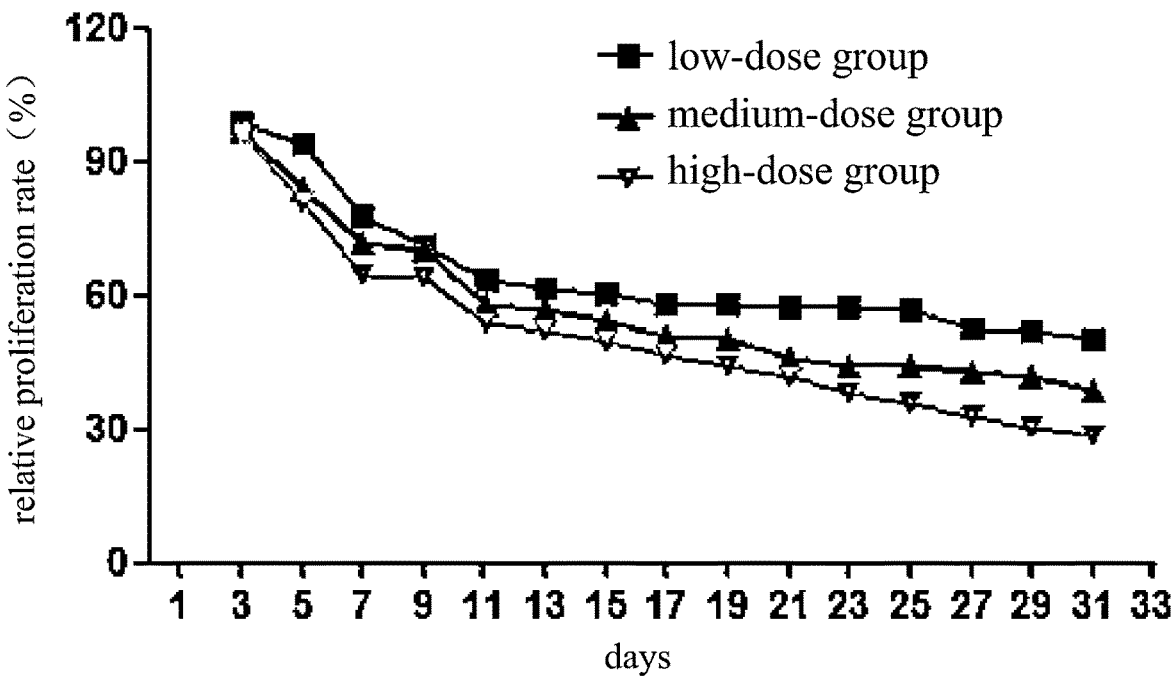
Figure 3C:
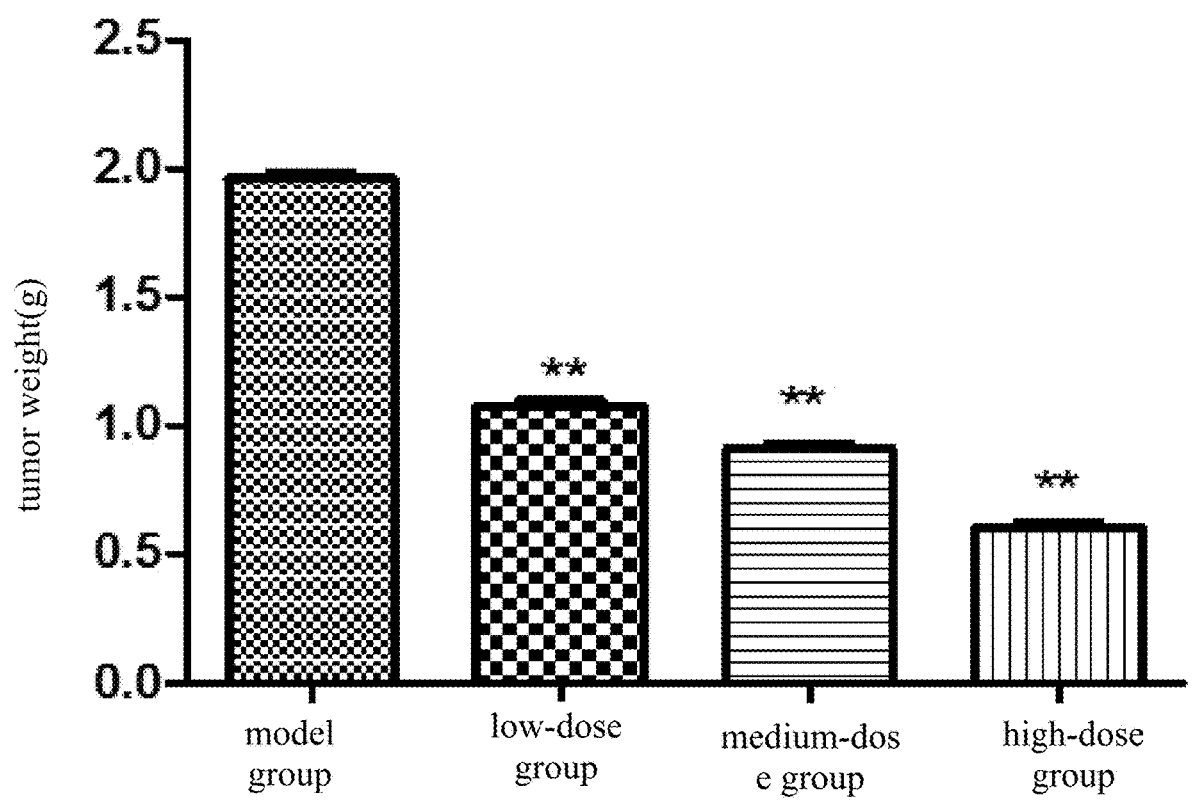
Figure 3D:
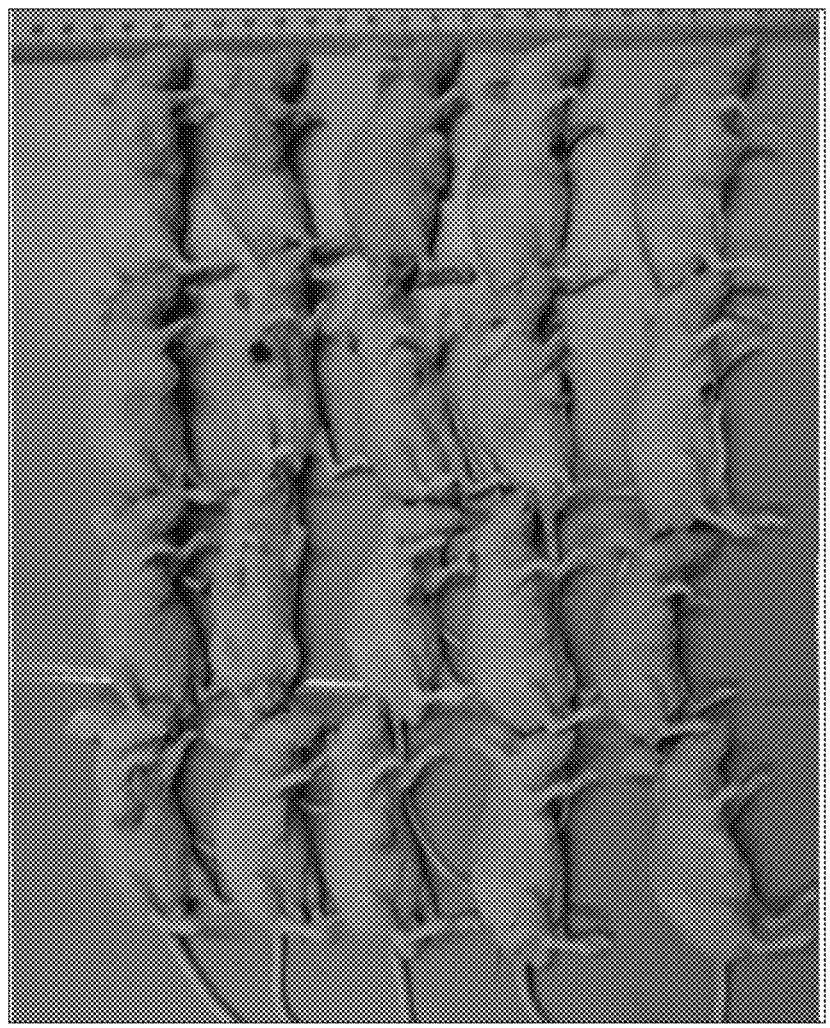
Figure 3E:
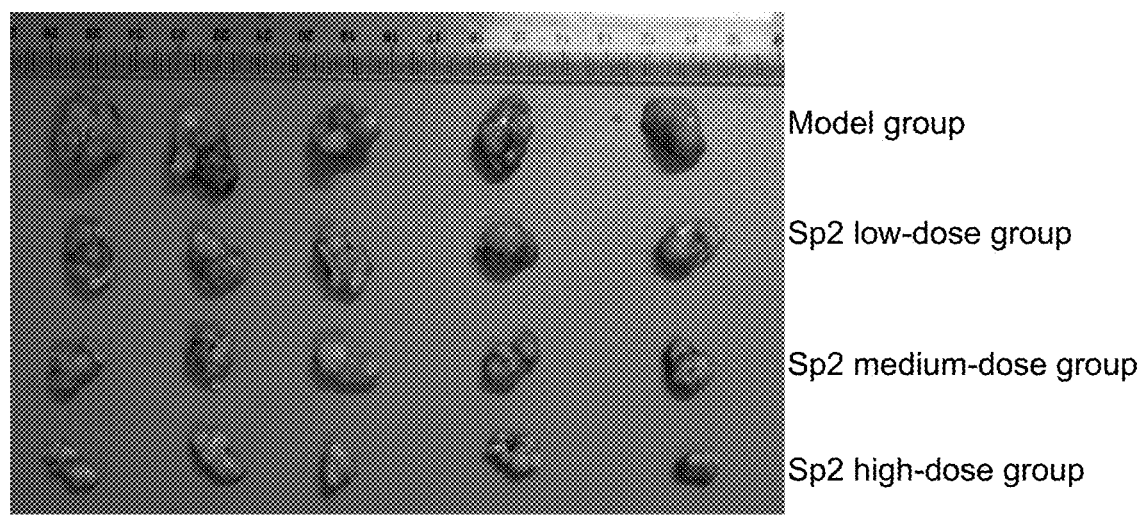

Cells were digested and counted to prepare a cell suspension with a concentration of $1 \times 10^5$ cells/mL. 100 μL of the cell suspension was added to each well of a 96-well plate ($1 \times 10^4$ cells per well); the 96-well plate was placed in a 37° C., 5% $CO_2$ incubator for 24 h; 100 μL of the corresponding drug-containing medium was added to each well, and a negative control group, a menstruum control group, and a positive control group were set up at the same time with 5 replicate wells in each group; the 96-well plate was placed in a 37° C., 5% $CO_2$ incubator for 72 h; 10 μL of CCK-8 solution was added to each well, and the culture plate was incubated in the incubator for 4 h; the OD value at 450 nm was measured with a microplate reader to calculate the inhibitory rate and $IC_{50}$ value of sp2 on BxPC-3 tumor cell lines. The evaluation standard plotted different concentrations of the same sample versus the tumor cell inhibition rate to obtain a dose-effect curve, and then the half effective concentration ($IC_{50}$ value) was calculated using the Logit method to, as shown in FIG. 2.

Inhibition rate and $IC_{50}$ value (%) of sp2 on the in vitro proliferation activity of in situ human pancreatic cancer cell BxPC-3

| Groups | BxPC-3, 72 hours | | |
|---|---|---|---|
| | OD | SD | Inhibition rate (%) |
| Negative control group | 1.299 | 0.082 | — |
| Menstruum control group | 1.279 | 0.025 | 1.56 |
| Positive control group | 0.295 | 0.046 | 77.32 |
| $IC_{50}$ = 23.39 μM 100 μM | 0.378 | 0.023 | 70.92 |
| 50 μM | 0.495 | 0.033 | 61.89 |
| 25 μM | 0.609 | 0.036 | 53.12 |
| 12.5 μM | 0.635 | 0.016 | 51.09 |
| 6.25 μM | 1.102 | 0.037 | 15.18 |
| 3.125 μM | 1.159 | 0.022 | 10.78 |
| 1.5625 μM | 1.222 | 0.026 | 5.93 |
| 0.78125 μM | 1.250 | 0.029 | 3.79 |
| 0.390625 μM | 1.258 | 0.044 | 3.19 |
| 0.1953125 μM | 1.278 | 0.019 | 1.62 |

Example 3

In Vivo Efficacy Evaluation of Sp2 on Human Pancreatic Cancer In Situ, Human Cervical Cancer, Human Ovarian Cancer, Human Osteosarcoma, and Human Poorly Differentiated Pregastric Cancer Subcutaneously in Nude Mice I. Cell lines: human cervical cancer cell line SiHa, human ovarian cancer cell line A2780, human pancreatic cancer in situ BxPC-3, human poorly differentiated pregastric cancer BGC-823, and human osteosarcoma cell line MG-63 were cultured in the RPMI-1640 medium containing 10% fetal bovine serum.

II. Modeling method: subcutaneous injection of cell line, tumor formation in the armpit III. Experimental steps:

(I) Cell Preparation Stage
1. The MG-63 cell lines in a good state of recovery was inoculated into a T75 cell culture flask and cultured at 37° C., 5% $CO_2$.
2. The medium was changed every 2-3 days, and when the cell healing degree reached about 80%, a 1:3 passage was performed, and about 20 bottles were needed.
3. After the number of cells was subcultured enough, the cells were collected by digestion and centrifugation, and the cell concentration was adjust to $5*10^7$ cells/mL with saline and got ready to inoculate nude mice.

(II) Animal Preparation Stage
1. Bclb/c nude mice of about 4 weeks were bought, and after a week of adaptive culture, the nude mice were ready to inoculate cells
2. Under aseptic conditions, a 1 mL syringe was used to suck up the cell suspension (during this period, it need to be shaken repeatedly to avoid cell sedimentation)
3. The nude mice were taken out, the inoculation site was wiped with alcohol (under the armpit of the right forelimb), and 100 uL of cell suspension (about $5*10^6$ cells/mouse) was inoculated in the biological safety cabinet with 30/each
4. After the cells were inoculated, the mice were put back into breeding under a condition of 25° C., alternate illumination every 12 hours, food and water were given as usual.
5. About five days after the inoculation, the inoculation site was touched to confirm whether there were nodules. If there was no nodule, the cells were replanted with double cell inoculation amount.
6. On day 8 after inoculation, the diameter of the transplanted tumor was measured using a vernier caliper and the tumor volume was calculated. When the tumor volume grew to 80-100 mm³, group administration (III) Animal Grouping and Number of Animals: 6/Group, 5 Groups in Total;
1. Model group: equal volume of NS, 0.1 mL/10 gBW;
2. Positive control group: 10 mg/kgBW of taxol;
3. Sp2 high-dose group: 16 mg/kgBW of sp2;
4. Sp2 medium dose group: 8 mg/kgBW of sp2;
5. Sp2 low-dose group: 4 mg/kgBW of sp2;

(IV) Animal Handling:
1. After the animals were grouped, the animals in each group were injected into the tail vein once a day, and they were given NS and high, medium and low doses of sp2 respectively for 4 weeks; taxol was administered twice a week for 4 weeks;
2. Starting from the grouping, the tumor size and weight were measured on the same day and every other day, the calculation formula of tumor volume (TV):

$$TV=0.5*a*b^2,$$

a was the long diameter and b was the short diameter;
3. The relative tumor volume (RTV) for each measurement was calculated, the calculation formula was:

$$RTV=Vt/V_0$$

wherein, $V_0$ represents the tumor volume measured in cage administration (i.e., $d_0$), and Vt represents the tumor volume at each measurement.
4. According to the relative tumor volume, the relative tumor proliferation rate T/C (%) was calculated:

the calculation formula was:

$$T/C\%=TRTV/CRTV*100\%.$$

5. After the experiment, the nude mice were killed by cervical dislocation method, and photographed according to different groups for records; the axillary tumor was peeled off, and photographed according to different groups, and the tumor was weighed.
6. Tumor growth inhibition rate (%) was calculated based on the tumor weight data Tumor growth inhibition rate %=(1−tumor weight of the experimental group/tumor weight of the control group)*100%

In vivo efficacy evaluation of sp2 on xenograft tumor subcutaneously in nude mice: the following table was based on T/C % and tumor growth inhibition rate (%);

Relative Tumor Growth Rate T/C (%)

| tumor type | T/C (%) |
| --- | --- |
| human cervical cancer SiHa in nude mice | 28.7 |
| human pancreatic cancer in situ in nude mice BxPC-3 | 31.0 |
| human ovarian cancer A2780 in nude mice | 34.3 |
| human osteosarcoma MG-63 in nude mice | 37.55 |
| human poorly differentiated pregastric cancer BGC-823 in nude mice | 42.09 |

Note:
according to the evaluation criteria of the efficacy of cytotoxic anti-tumor drugs: T/C % >40% was invalid; T/C % ≤40% with statistically processed P < 0.05 was effective.

According to the evaluation criteria of the efficacy of non-cytotoxic anti-tumor drugs: T/C %>60% was invalid; T/C %≤60% with statistically processed P<0.05 was effective.

Tumor Growth Inhibition Rate (%) was Calculated According to Tumor Weight

| tumor type | inhibition rate (%) |
| --- | --- |
| human cervical cancer SiHa in nude mice | 69 |
| human pancreatic cancer in situ in nude mice BxPC-3 | 66 |
| human ovarian cancer A2780 in nude mice | 58.5 |
| human osteosarcoma MG-63 in nude mice | 57.3 |
| human poorly differentiated pregastric cancer BGC-823 in nude mice | 56.8 |

Note:
evaluation criteria of the efficacy: inhibition rate (%) <40% was invalid; inhibition rate (%) ≥40% with statistically processed P < 0.05 was effective (FIGS. 3a-3e).

Example 4

Efficacy Experiment of sp2 In Situ Inoculation on Nude Mice with A549-luc Cells

Cell line: human lung adenocarcinoma cell A549-luc (A549 cells with luciferase)

Figure 4A:
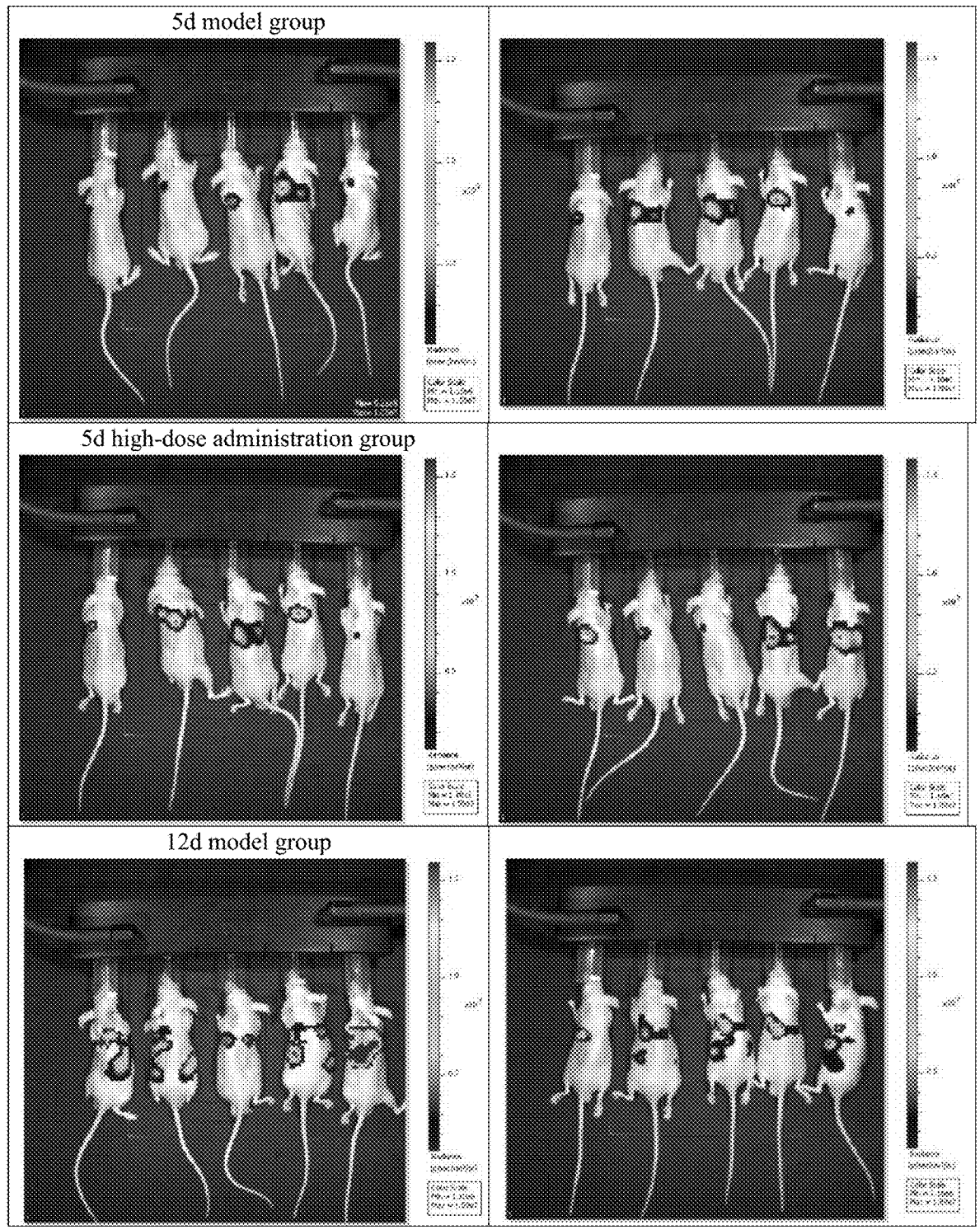
FIGS. 4a and 4b. In vivo efficacy of sp2 on the xenograft tumor of nude mouse human lung adenocarcinoma in situ A549, wherein, FIG. 4a. In vivo imaging fluorescence intensity comparison of sp2 on in vivo efficacy of nude mouse human lung adenocarcinoma in situ A549.
Figure 4A:
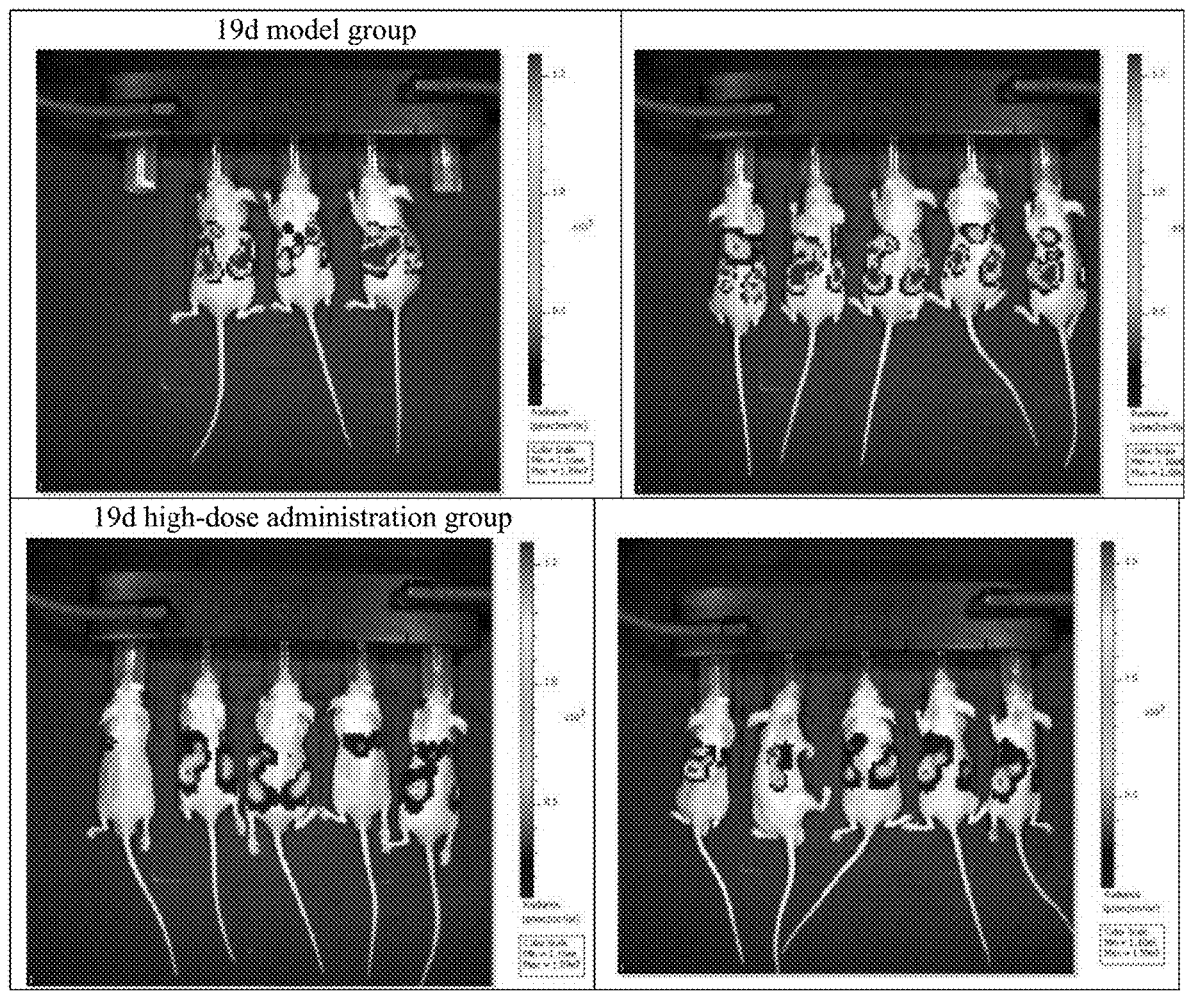
Figure 4B:
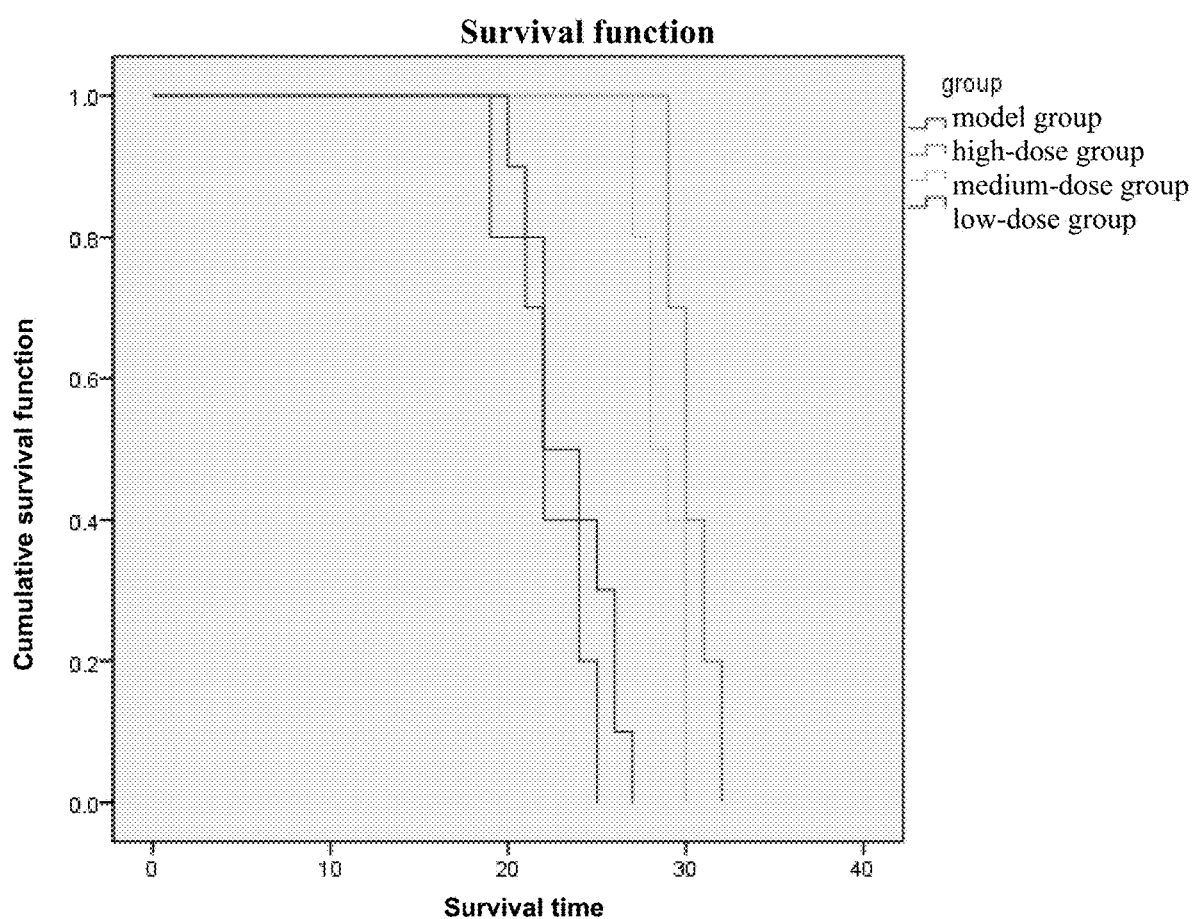

Animals: male Balb/c nude mice, 6 weeks old, weight<20 g;

1. Inoculating Method:
Cell preparation: A549-luc cells were resuscitated and passaged, resuspended in PBS and mixed with matrigel at a ratio of 1:1. The lungs of each nude mouse was injected with 100 μL of the mixed suspension containing $5\times10^6$ cells 1) Anesthesia: after the animal was anesthetized, it was placed on a clean bench and fixed, and the surface of the chest cavity was disinfected with iodine and alcohol.
2) Position determination: it was located about 1 cm above the lower edge of the mouse left costal arch (between the fourth and fifth costal arches), where there were two thick longitudinal blood vessels. The lung was located between these two blood vessels and marked with a marker pen.
3) Exposing the lung: first the epidermis was cut a small opening of about 5 mm, and the lower subcutaneous and muscle tissue along this small opening were gradually cut. The pink lung could be seen across the pleura, and the lung would expand and shrink with the breathing movement of the mouse.
4) Tumor cell injection: a mixed 100 μL of the mixed cell suspension (cell suspension+matrigel) was taken and slowly injected into the lung of the mouse along the opening.
5) The cut mouse epidermis was sutured, and the mouse was placed on a 37° C. constant temperature heating plate until the mouse awoke, and then returned to the original cage to continue feeding. The wound could heal in 4-6 days.
6) Observation of Tumor Growth
   a. Cells was inoculated into each nude mouse, starting from the day of modeling, i.e., day 0, and imaging the nude mice in vivo every 7 days from day 4;
   b. The tumor size and metastasis of each group of mice (whether there was metastasis, and where it metastasized) were observed,
   c. The mice were weighed. The death time of the animal was observed and recorded, and the survival days were calculated.
2. In Vivo Imaging Observation Method
Each nude mouse was intraperitoneally injected with 150 μL of luciferase substrate. After the mouse was acted with the substrate for 5 min and anesthetizes for 5 min, it was put into the main box of the in vivo imaging instrument for shooting. T/C (%) was obtained by statistical processing
3. Method of Administration:
After in situ inoculation, the tail vein administration was started on day 4, once a day, for 3-4 weeks.
4. Test drug: sp2
5. Grouping: model group, high-dose, medium-dose, low-dose; 10 nude mice per group;
6. Results analysis:
1) the median survival time of nude mice in sp2 high, sp2 medium and sp2 low-dose groups were 30.3 d, 28.7 d, and 23.5 d, respectively. Compared to the model group, the difference in median survival time between the high and medium concentrations of sp2 was statistically significant (P<0.05),
2) tumor metastasis observation
Model group:
on day 5, tumor fluorescence was mainly concentrated in the lungs, and no extrapulmonary metastasis was found;
on day 12, the tumor fluorescence signal of 3 nude mice increased further, and the tumors of the other 7 nude mice developed extrapulmonary metastasis;
on day 19, 2 nude mice die, 8 surviving mice had extensive metastasis, and the fluorescence signal was very strong;

sp2 high concentration group:
On day 5, tumor fluorescence was mainly concentrated in the lungs, and no extrapulmonary metastasis was found;
on day 12, tumor fluorescence was still concentrated in the lungs, there was no extrapulmonary metastasis, and the tumor fluorescence signal was significantly enhanced;
on day 19, no extrapulmonary metastasis was seen in 2 nude mice, and extrapulmonary metastasis was seen in the other 8 nude mice,
on day 26, no extrapulmonary metastasis was seen in 2 nude mice, and extrapulmonary metastasis was seen in the other 8 nude mice, and the tumor fluorescence signal further increased (FIGS. 4a and 4b).

Example 5

Efficacy Test of sp2 on Human Pancreatic Cancer In Situ BxPC-3 Cells Orthotopically Inoculated in Nude Mice
Cell line: human pancreatic cancer cell BxPC-3;
Construction of Luc-containing lentiviral vector: lentiviral packaging;
Transfecting BxPC-3 cells and screening stable transgenic strains;
Animals: male Balb/c nude mice, 5 weeks old, weight<20 g;
Method of In Situ Inoculation:
cell preparation: BxPC3-luc cells were resuscitated and passaged. When the cells cultured in vitro were in the logarithmic growth phase, they were trypsinized to prepare a single cell suspension, and the cell concentration was adjusted to $1\times10^7$ cells/mL.
1) Anesthesia: after the animal was anesthetized, it was placed on a clean bench and fixed, and the and surface of the chest cavity and abdomen was disinfected with iodine and alcohol.
2) Tumor cell injection:
The membrane between the stomach and the spleen was separated to expose the pancreas, and 50 uL of the cell suspension was injected under the pancreatic capsule
3) After the incision skin was sutured, and the mouse was placed on a 37° C. constant temperature heating plate until the mouse awoke, and then returned to the original cage to continue feeding.
In Vivo Imaging Observation Method
1) Cells was inoculated into each nude mouse, starting from the day of modeling, i.e., day 0, and imaging the nude mice in vivo every 7 days from day 3 for 4 weeks;
2) Each nude mouse was intraperitoneally injected with 150 μL of luciferase substrate. After the mouse was acted with the substrate for 5 min and anesthetizes for 5 min, it was put into the main box of the in vivo imaging instrument for shooting.
Method of Administration:
After in situ inoculation, the tail vein administration was started on day 3, once a day, for 4 weeks.
Test drug: sp2;
Grouping: model group, positive control taxol group, high-dose, medium-dose, low-dose; 10 nude mice per group
Observation of Tumor Growth:
a. The tumor size and metastasis of each group of mice (whether there was metastasis, metastasis location) were observed through in vivo imaging;
b. changes in animal weight were observed and recorded, and weight change curves were drawn;

c. The death time of the animal was observed and recorded, and the survival days were calculated.
d. When the animal died or executed after the experiment was completed, all the test animals were generally dissected.

In vivo imaging fluorescence intensity comparison; different doses of sp2 and positive control taxol acted on pancreatic cancer in situ model nude mice, and the statistical result after in vivo imaging detection was as follows: compared to the model group, the average fluorescence intensity of the sp2 high-dose group on days 10, 17, and 24 was significantly reduced (P<0.05); the sp2 medium-dose group was also significantly reduced on day 17; the inhibitory effect of sp2 had a significant dose-response relationship, and there was no significant difference in the inhibitory effect of sp2 on pancreatic cancer compared to the positive control itaxol group (P>0.05) (FIG. 5).

Example 6

Activity Detection of Solid Tumor Telomerase
1. Sample preparation: tumor samples of human cervical cancer, human ovarian cancer, human pancreatic cancer, human osteosarcoma, and human poorly differentiated pregastric cancer taken at the end of the anti-tumor efficacy experiment in nude mice
2. Extraction of total RNA
3. Reverse transcription of RNA into cDNA
4. QPCR reaction: the operating method of AppliedBiosystems7500 was used
   1) Preparation of PCR reaction solution
   Usually a final primer concentration of 0.2 μM could obtain better results. The primer concentration could be adjusted within the range of 0.1 to 1.0 μM.
   2) ROX Reference DyeII (50×) has a lower concentration than ROX Reference Dye (50×). When using 7500 Real-Time PCR System and 7500 Fast Real-Time PCR System, ROX Reference DyeII (50×) was used. When using ABIPRISM 7300 Real-Time PCR System and Step One Plus™, ROX Reference Dye (50×) was used.
   3) In a 20 μL reaction system, the amount of DNA template added was usually below 100 ng. Because different types of DNA templates contained different copy numbers of target genes, if necessary, gradient dilutions could be performed to determine the optimal DNA template addition amount.
   4) The reaction solution was prepared according to the recommended system of each instrument.
   5) Real Time PCR reaction was carried out: the two-step method adopted the standard PCR amplification procedure.
   6) Analysis of experimental results (FIG. 6).

Example 7 sp2 Induced Human Acute Myeloid Leukemia HL-60 Cell Line to Differentiate into Normal Granulocytes.

The method of sp2 inducing human acute myeloid leukemia HL-60 cell line to differentiate into normal granulocytes:
1. Cell culture: cells: HL-60 cell line was cultured in RPM11640 medium containing 15% fetal bovine serum at 37° C., 5% $CO_2$ under saturated humidity. Cells in the logarithmic growth phase were taken for experiment.
2. Preparation of sample sp2 stock solution: 3000 μg/bottle of sp2 lyophilized powder was dissolved in 0.97 mL ultrapure water (its concentration was 2000 μM, i.e., 3105 μg/mL), which was equivalent to 10 times the working solution concentration of the high-dose group (200 μM, i.e., 310.5 μg/mL);
(1) Grouping: control group, sp2 administration group; (2) dose setting of administration group, from 25 to 200 μM (dose groups 1-4).

sp2 was prepared into four working solutions of 200, 100, 50 and 25 μM with culture medium: (3) different concentrations of sp2 were co-cultured with HL-60 cell line ($10^6$/mL) in the logarithmic growth phase for 5 days. It was passaged for 24-48 h to keep the cells in the logarithmic growth phase. The control group was added with the same volume of solvent as the administration group.

7a. Cell Cycle Arrest
The cell cycle reflected the cell proliferation rate. Propidium Iodide (PI) is a fluorescent dye for double-stranded DNA. The combination of propidium iodide and double-stranded DNA can produce fluorescence, and the fluorescence intensity is proportional to the content of double-stranded DNA. After the DNA in the cell is stained with propidium iodide, the DNA content of the cell can be determined with a flow cytometer, and then cell cycle analysis can be performed according to the distribution of the DNA content.
(1) Cell culture
(2) The cultured cells of different groups were digested with 0.25% trypsin to make them into single cells. The cell suspension was mixed thoroughly by pipetting and collected in a dedicated flow tube;
(3) The cell suspension was centrifuged at 1000 g for 5 min, and the supernatant was absorbed and discarded; the precipitate was suspended in 300 μL of PBS solution containing 10% fetal bovine serum and transferred to a clean 1.5 mL centrifuge tube;
(4) The tube was added with 700 μL of absolute ethanol, and place in a refrigerator at −20° C. to fix the cells for more than 24 h;
(5) The fixed sample was taken out, and centrifuged at 3000 g for 30 sec. The supernatant was absorbed to remove;
(6) The cell precipitation was dissolved and suspended with 100 μL of RNaseA at a concentration of 1 mg/mL, and the RNA in the cells was digested in an incubator at 37° C.;
(7) 400 μL of propidium iodide (PI) solution with a concentration of 50 μg/mL was added, and the nucleus was stained for 10 min in the dark. Flow cytometry was used to determine the cell DNA content to determine the proportion of cells in each cell cycle;

FIG. 7a. shows a result of FCN detection: the effect of different doses of sp2 on the cell cycle of HL-60; A. control group, B. 25 μM, C. 50 μM, D: 100 μM, E: 200 μM.

TABLE 1

Cell cycle after the human promyelocytic leukemia cell line HL-60 was treated with different concentrations of sp2

| Sample | DipG1 (%) | DipG2 (%) | DipS (%) | G2/G1 | % CV | TotalS-Phase (%) |
| --- | --- | --- | --- | --- | --- | --- |
| NC | 41.43 | 14.29 | 44.29 | 2.00 | 4.70 | 44.29 |
| sp2, 25 uM | 58.32 | 9.36 | 32.33 | 2 | 5.34 | 32.33 |
| sp2, 50 uM | 58.85 | 8.67 | 32.48 | 2 | 5.14 | 32.48 |
| sp2, 100 uM | 59.64 | 14.72 | 25.64 | 1.92 | 4.95 | 25.64 |
| sp2, 200 uM | 63.58 | 7.22 | 29.20 | 2.00 | 4.61 | 29.20 |

Compared with the control group, it showed a G1 phase arrest after treated with sp2;

FCM detection of cell cycle: after the human promyelocytic leukemia cell line HL-60 was treated with different concentrations of sp2, the expression of cells in G0/G1 phase increased, the expression of cells in S phase decreased, and the expression of cells in G2 phase decreased, showing a G1 phase arrest with a dose-response relationship;

7b. HE Staining (Suspension Cell) Method;
(1) 95% ethanol was used to wipe or soak a new glass slide that was degreased, dry, clean, oil-free, and scratch-free to prepare a smear;
(2) the cell suspension was centrifuged at 4° C. for 30 min, the supernatant was removed and a small amount of the supernatant was left for subsequent smears;
(3) in the biological safety cabinet, about 0.05 mL-0.1 mL of the mixed cell suspension sample was drawn using a pipette, evenly smeared on the front surface of the glass slide into a 10 mm×20 mm oval membrane, and placed on a baking sheet machine to dry;
(4) fixed in 10% neutral formalin for 10 min;
(5) washed with water for 2 min;
(6) stained with hematoxylin semen for 1-2 min;
(7) washed away free hematoxylin with running water for 5-10 S;
(8) treated with 1% hydrochloric acid alcohol for 1-3 S;
(9) washed with water for 1-2 S;
(10) returned to blue with blue promoting liquid for 5-10 S;
(11) washed with running water for 15-30 S;
(12) stained with 0.5% eosin solution for 2-3 min;
(13) washed with distilled water for 1 min;
(14) treated with 80% ethanol for 1-2 S;
(15) treated with 95% ethanol for 1-2 S;
(16) treated with absolute ethanol 1-2 S;
(17) treated with xylene I for 2-3 S;
(18) treated with xylene II for 2-3 S;
(19) sealed with neutral gum.

HE staining (suspension cell) results and analysis:

FIG. 7b shows the effect of sp2 on the percentage (%) of mature and immature cells of HL-60 (human acute myeloid leukemia) cells.

| No. | Mature cells (%) | Immature cells (%) |
|---|---|---|
| C (control) | 40.1 | 59.9 |
| sp2, 25 μM | 49.6 | 50.4 |
| sp2, 50 μM | 42.0 | 58.0 |
| sp2, 100 μM | 69.2 | 30.8 |
| sp2, 200 μM | 85.6 | 14.4 |

7c. Blue Tetrazolium (NBT) Reduction Reaction Test:
(1) the cell suspension of each group was collected, centrifuged, and added with 0.5 mL of 0.1% NBT and 100 μL of 200 mg/L TPA to mix well;
(2) the mixture was incubated at 37° C. for 3 h;
(3) the reaction was terminated by centrifugation; the cell suspension was fixed for 10 min with formaldehyde, and smeared;
(4) giemsa staining for 5 min;
200 cells were counted and the percentage of positive cells was calculated.

FIG. 7c is the detection of the in vitro differentiation effect of different doses of sp2 on HL-60 (NBT reduction reaction, counting 200 cells)

| Sample No. | Rate of positive cells (%) | Multiple of photo |
|---|---|---|
| NC | 6 | 200 |
| sp2, 25 μM | 72 | 200 |
| sp2, 50 μM | 73 | 200 |
| sp2, 100 μM | 76.5 | 200 |
| sp2, 200 μM | 81 | 200 |

The above results indicated that, compared to the control group, the rate of NBT-positive cells in the human promyelocytic leukemia cell line HL-60 increased significantly after treated with sp2, which had a dose-effect relationship. It showed that sp2 could effectively improve the NBT reduction ability of HL-60 and induce differentiation of HL-60 cells (FIG. 7b).

After the cells became cancerous, the phenotype of tumor cells returned to an undifferentiated state. After sp2 was incubated with HL-60 for 5 days, the cell cycle of HL-60 cells showed a significant G1 phase arrest, the cell morphology changed from immature to mature, and NBT reduction ability was enhanced. It showed that cell proliferation to differentiation was a process of cell cycle arrest and activation to induce differentiation (morphological and functional changes), and sp2 played a significant role in promoting differentiation of tumor cells (FIGS. 7a-7c).

Example 8 sp2 Promoted Tumor Cell Apoptosis of Tumor-Bearing Nude Mice

1. Tumor-bearing human tumorigenic osteosarcoma MG-63 and human poorly differentiated pregastric cancer BGC-823 tumor tissues subcutaneously in nude mice administered with sp2 for 4 consecutive weeks were used to prepare a solid tumor single cell suspension, respectively;
1) The tumor block was washed 2-3 times with PBS buffer, cut into small pieces (1-2 mm$^3$) with ophthalmic surgical scissors, then washed 2-3 times with PBS, and transferred to a 50 mL centrifuge tube.
2) 5-6 times of 0.25% pancreatin solution was added according to the amount of tissue block to digest at 37° C. for 20-40 min, and the tube was gently shaken every 5 min to separate the cells.
3) 2-5 mL of serum-containing medium was added to stop trypsin digestion.
4) The suspension was let stand for 2-3 min, transferred to a new centrifuge tube, and filtered twice with a 200-mesh nylon mesh.
5) The filtered suspension was centrifuged at 1000 rpm for 5 min, and the supernatant was discarded.
6) 5 mL of PBS buffer was slowly added to the cells, and centrifuged again. The supernatant was discarded.
7) 1-2 mL of culture medium was added according to the amount of cells, and the cells were counted for use.

2. AnnexinV-FITC cell apoptosis (annexinV)
1) The solid tumor single cell suspension was added with cell culture medium, mixed well, transferred to a centrifuge tube, and centrifuged at 1000 g for 5 min. The supernatant was discarded, and the cells were collected, which was resuspended gently with PBS and counted.
2) 50,000-100,000 resuspended cells was taken, and centrifuged at 1000 g for 5 min. The supernatant was discarded, and 195 μl of AnnexinV-FITC binding solution was added to gently resuspend the cells.

3) 5 μl of AnnexinV-FITC was added and mixed gently.
4) 10 μl of propidium iodide staining solution was added and mixed gently.
5) The suspension was incubated at room temperature (20-25° C.) in the dark for 10-20 min, and then placed in an ice bath. Aluminum foil could be used to protect from light. Cells could be resuspended 2-3 times during incubation to improve the labeling effect.
6) Immediately flow cytometry detection was performed, wherein AnnexinV-FITC was green fluorescence, and PI was red fluorescence.

Test results of tumor cell apoptosis: compared to the model group, the taxol group could increase the tumor cell apoptosis rate (P<0.05); compared to the model group, each dose group of sp2 had a pro-apoptotic effect, and compared to the positive control taxol group, there was no significant difference between the sp2 high and low dose groups and the positive control taxol group (P>0.05) (FIG. 8).

Example 9

Flow Cytometric Detection of T Cell Content in Peripheral Blood
1. Reagents and Antibodies

| Reagent name | Factory | Catalog No |
| --- | --- | --- |
| CD3-FITC flow cytometric antibody | BD | 553061 |
| CD4-APC flow cytometric antibody | BD | 553051 |
| CD8-PE flow cytometric antibody | BD | 553032 |
| CD19PE-cy7 flow cytometric antibody | BD | 552854 |

2. Experimental Methods and Results
1) Before death of the tumor-bearing nude mice by cervical dislocation method, the eyeballs were removed to take anticoagulant blood, which was stored at 4° C. for use (detection was completed on the day);
2) Centrifuging slightly to allow the cells to settle to the bottom of the tube, and 100 μL of whole blood was taken. 10 μL of the corresponding antibody was added to each tube, protected from light at room temperature for 20 min after shaking;
3) 1 mL of hemolysin was added, and protected from light for 10 min after shaking;
4) Centrifuged at 1200 rpm for 5 min; the supernatant was removed and the precipitate was shaken;
5) 2 mL of PBS washing solution was added, shaken and centrifuged at 1200 rpm for 5 min; the supernatant was removed and the precipitate was shaken;
6) 500 μL of PBS was added and stored at 4° C. before testing;
7) Test;
8) Result analysis: the taxol group showed obvious toxicity to T lymphocytes, and there was a significant difference (P<0.01) compared to the model group; as the dose of sp2 increases, there was a tendency to promote the increase of T lymphocytes, but there was no significant difference compared to the model group (P>0.05); compared to the taxol group, the sp2 high-dose group could promote increase of the content of T lymphocyte (P<0.05) (FIG. 9).

Example 10 sp2 can Promote the Transformation of Nude Mouse Splenic Lymphocytes
1. Preparation of Spleen Cell Suspension
1) After the nude mice were killed by cervical dislocation method, they were immersed in 75% alcohol for 10 min, and dissected in a biological safety cabinet. The spleen was separated and placed in a small plate containing an appropriate amount of sterile PBS.
2) After the spleen was washed with PBS, it was cut into small pieces of 1 mm$^3$ using surgical scissors, and filtered with a 200-mesh sieve, and the spleen tissue was ground with the rubber part of the injection rod of the syringe, and washed with PBS and collected the supernatant.
3) The supernatant was centrifuged at 1500 rpm/min for 5 min, and washed with PBS (without calcium and magnesium ions) for 1-2 times.
4) The cells were added with 4 mL of erythrocyte lysate, resuspended, reacted at 37° C. for 5 min, and centrifuged (1500 rpm, 5 min). The supernatant and was discarded.
5) After the cells were washed with PBS once, they were resuspended in complete medium and counted, and adjusted to a concentration of $10^6$ cells/mL.
6) The cell suspension was added to a 96-well plate with 100 μL/well, and adaptive cultured for 4 h;
7) Fresh culture medium was replaced, wherein ConA (final concentration 5 μg/mL) was added to the experimental group, and the same volume of culture medium was added to the control group, and cultured for 48 h.
8) 10 μL of CCK-8 solution was added to each well, and incubated in the incubator for 4 h. The absorbance at 450 nm was measured with a microplate reader, and the proliferation rate was calculated. The OD values of the three replicate wells of the experimental group and the control group were averaged.

Conversion value=average OD value of the experimental group–average OD value of the control group.

T lymphocyte transformation results: compared to the model group, the taxol group significantly reduced the T lymphocyte transformation efficiency (P<0.01); compared to the model group, the T lymphocyte transformation efficiency of each dose group of sp2 was better than that of the model group, wherein there was no difference in the low-dose group (P>0.05), and there was significant difference in the medium-dose group and the high-dose group (P<0.01); compared to the taxol group, each group could significantly improve the transformation efficiency of T lymphocytes after sp2 administration for 4 weeks (P<0.01) (FIG. 10).

Example 11

Immunofluorescence Test was Used to Detect the Inhibitory Effect of sp2 on PD-L1 and CD47
1. Sample of human cancer xenograft tumor tissue subcutaneously in tumor-bearing nude mice
2. Antibody

| Antibody | Source | Manufacturer | Cargo No. |
| --- | --- | --- | --- |
| PD-L1 | Rabbit | Abcam | Ab213480 |
| CD47 | Rabbit | proteintech | 18470-1-AP |

Experimental Steps:
1, Preparation of tissue sections
   1.1 the slicing knife was installed on the knife holder of the blade machine and fixed tightly. The wax block base was fixed, and the blade and the surface of the wax block were adjusted to have an angle of 5 degrees;
   1.2 the thickness of the section was 4-7 μm;
   1.3 flatting and taking out the section: the section flatten machine was used, and first the water temperature was kept at 45-50° C.; the section was gently held up using a brush with your left hand, and a corner of the section was held up using tweezers with your right hand, and the section was gently placed on the water surface of the section flatten machine with the front facing up; after the paraffin section floated in warm water and was heated, it flatted naturally and smoothly under the action of surface tension, and then the section was taken out and numbered;
   1.4 baking the section: after the flatten section was slightly dried at room temperature, the section was placed in a constant temperature oven at 40° C. for 0.5-2 h to dry for use;
2, Tissue dewaxing and hydration
3, Antigen retrieval The section was placed in a container filled with citrate buffer (0.01 mol/L, pH 6.0), and heated in a microwave oven (microwave 3 levels) to maintain the liquid in the container at about 98° C. for 10-15 min. The container was taken out and cooled at room temperature for 20-30 min (Note: do not remove the section from the buffer to cool, so that the protein can restore the original spatial configuration). The section was washed with PBS for 3 times, and 5 min each time; after hot steam retrieval for 20 min, the section was naturally cooled to room temperature.

4, The PBS was removed, and the section was blocked with 5% BSA/0.01 M PBS for 30 min without washing, and absorbent paper was used to remove the 5% BSA blocking solution from the edge. The diluted antibody solution (diluent was PBS containing 5% BSA) was added dropwise; in the blank control group, PBS (0.01M, pH=7.4) was used to replace the antibody and incubated in a wet box at 4° C. refrigerator overnight.

5, The next day, the wet box was taken out from the refrigerator, and placed at room temperature for 15 min to rewarm. The section was washed with PBS 5 times for 5 min each time. The surplus PBS was absorbed, fluorescent secondary antibody was added dropwise, and incubated at room temperature in the dark for 30 min, then the section was washed with PBS 5 times for 5 min each time.

6, DAPI was added dropwise to incubate for 2 min in the dark, and nucleation were revealed and blue fluorescence was observed. The section was washed with PBS 3 times for 1 min each time.

7, The section was blocked with glycerol and observed immediately under a fluorescence microscope.

8, Analysis

9, Average optical density (OD) and positive area ratio (positive area/total area) were calculated.

Positive index=positive area ratio×OD

The result showed that sp2 significantly enhanced the immune effect of tumor-bearing nude mice to eliminate tumor cells Example 12

Animal Acute Toxicity Test of sp2 (Upper and Lower Method)

Limit experiment of 2000 mg/kgBW dose level.

Characteristics of the method: The number of animals used is small, the $LD_{50}$ value can be estimated, and the toxicity performance can be observed.

1. Test substance: sp2.
   Content (or specification): the sample was accurately divided with 40 mg/bottle*5 bottles.
   Storage conditions: being stored at −20° C.
   Sample purity: HPLC detection purity>98.5%.
   Preparation method: 40 mg/1.5 mL ultrapure water.
   Route of administration: mouse tail vein injection.
   Administration method: animal acute toxicity test (single dose toxicity test) was to study the toxic reaction of the animal within a certain period of time after the animal was given the test substance once or multiple times within 24 h. In this experiment, three doses within 24 h were used, namely 0.5 mL/each, 3 times/day, with an interval of 3 h;
   Dosage: 2000 mg/kgBW.
2. Animals: male ICR mice, 6 weeks old, weight 20±2 g.
3. Experimental method:
   a. the test substance (sp2) was injected at a dose of 2000 mg/kgBW into the tail vein of an ICR mouse: the dose was calculated according to body weight; the tail vein injection volume of sp2 was 2 mg/0.075 mL/per gram of body weight;
   b. observing and recording whether there was a toxic reaction (initial symptoms, onset time was time after administration, severity and duration)
   c. if the animal died, the reaction before death and the time of death was recorded;
   d. if the animal was alive, the test substance was given to another 4 animals, at this time the total number of animals was 5. If only one of the five animals died in the later period of the experiment (i.e., the observation period), and the other four animals survived. Continuing to observe them, and the animals that died in the later period should be counted as the other dead animals;
4. The results were evaluated as follows:
   If the number of dead animals was ≥3, $LD_{50}$ was less than 2000 mg/kgBW; entering the main experiment (according to the "technical guidelines for acute toxicity tests of chemical drugs");
   If the number of surviving animals was ≥3, $LD_{50}$ was greater than 2000 mg/kgBW (the experimental design could estimate the $LD_{50}$ value);

The experimental result showed that in the 2000 mg/kgBW dose level group, when the sp2 test substance was injected into the tail vein of ICR mice at a dose of 2000 mg/kgBW, one of the mice showed an increase in sexual activity after the administration, and then the symptoms disappeared; within two weeks of observation, none of the experimental mice died.

According to the evaluation criteria of the limit test protocol, the number of surviving animals was ≥3, and $LD_{50}$ was greater than 2000 mg/kgBW.

TABLE 2

Acute toxicity test of Sp2 injected into the tail vein of ICR mice at a dose of 2000 mg/kgBW

| Number | Body weight | Toxic reaction manifestations (the symptoms of poisoning, the time of symptom onset, severity, and duration after administration) | Death (reaction before death, and death occurred within 2 weeks after administration) |
|---|---|---|---|
| 1 | 20.5 | No obvious abnormalities | Survival |
| 2 | 20.8 | No obvious abnormalities | Survival |
| 3 | 20.1 | An increase in sexual activity | Survival |
| 4 | 20.3 | No obvious abnormalities | Survival |
| 5 | 21.1 | No obvious abnormalities | Survival |

It was estimated that $LD_{50}$ of sp2 was greater than 2000 mg/kgBW.

Embodiment 13

Animal Acute Toxicity Test of sp2 (Maximum Dose Method)

I. Experimental Animals and Drugs
  Experimental conditions: GoodLaboratoryPractice, GLP
  1. Experimental animals
    20 Kunming mice, healthy adults, half male and half male, weight 20 g±2%
  2: Feeding conditions
  A constant temperature environment of 25° C., alternate illumination every 12 hours, in a sterile environment and the mice were given enough water and food.
  3: Test sample
    sp2 of synthetic peptide freeze-dried powder with a purity of >99.34%, and accurately divided into 40 mg per bottle, with a total of 40 mg/bottle*20 bottles
    Lot No: 04010039572, Suzhou Qiangyao Biological Technology Co., Ltd.

II. Acute Toxicity Test in Mice
  1. Experimental steps
    1) Kunming mice were weighed and recorded.
    2) The $sp^2$ freeze-dried powder was taken out from −20° C., and placed at room temperature for 15 min; the lid was carefully opened, and 1.5 mL of physiological saline was added to dissolve the powder completely by shaking.
    3) Dosage: 2000 mg/kgBW (sp2 concentration was 40 mg/1.5 mL, the dose for mice was according to volume=0.075 mL*mouse body weight);
    4) Route of administration: tail vein injection;
    5) Administration method: animal acute toxicity test with a single dose was to study the toxic reaction of the animal within a certain period of time after the animal was given the test substance once or multiple times within 24 h. In this experiment, 3 doses within 24 h were used, namely 0.5 mL/each, 3 times/day, with an interval of 3 h;
    The sp2 concentration was 40 mg/1.5 mL, and the dose per mouse was calculated according to volume=0.075 mL*mouse weight;
    6) Observing and recording the reaction symptoms of the test animals for 14 consecutive days with twice a day on the day of administration and the next day, and then once a day;
    7) At the end of the experiment, the animals were killed by cervical dislocation. All the test animals were dissected to observe whether their tissues and organs were changed in volume, color, texture, etc. and recorded;

TABLE 3

After injection of sp2 at a dose of 2000 mg/kgBW into the tail of Kunming mice, the animal weight changes were continuously observed

| Date No. | 1♂ | 2♂ | 3♂ | 4♂ | 5♂ | 6♂ | 7♂ | 8♂ | 9♂ | 10♂ | male |
|---|---|---|---|---|---|---|---|---|---|---|---|
| 1 d | 26.47 | 28.89 | 27.28 | 27.05 | 27.75 | 28.26 | 28.12 | 27.23 | 27.08 | 27.52 | 27.565 |
| 3 d | 29.58 | 31.85 | 31.36 | 29.93 | 31.82 | 32.19 | 32.01 | 30.82 | 30.72 | 31.03 | 31.131 |
| 5 d | 30.92 | 35.06 | 32.22 | 31.09 | 33.08 | 35.44 | 34.8 | 33.26 | 32.56 | 33.34 | 33.177 |
| 7 d | 33.72 | 37.68 | 34.7 | 33.27 | 36.87 | 37.79 | 36.92 | 35.14 | 34.02 | 36.88 | 35.699 |
| 9 d | 35.42 | 40.29 | 37.3 | 35.89 | 38.45 | 39.54 | 38.88 | 36.74 | 35.17 | 38.43 | 37.611 |
| 11 d | 35.39 | 42.97 | 37.68 | 36.62 | 38.95 | 39.82 | 38.98 | 36.45 | 35.03 | 38.28 | 38.017 |
| 13 d | 35.19 | 42.67 | 37.92 | 36.83 | 39.71 | 39.7 | 39.51 | 37.46 | 36.63 | 38.94 | 38.456 |

| Date No. | 11♀ | 12♀ | 13♀ | 14♀ | 15♀ | 16♀ | 17♀ | 18♀ | 19♀ | 20♀ | female |
|---|---|---|---|---|---|---|---|---|---|---|---|
| 1 d | 27.96 | 31.05 | 25.45 | 27.82 | 24.7 | 27.38 | 24.31 | 25.12 | 24.92 | 25.87 | 26.458 |
| 3 d | 30.25 | 32.03 | 27.59 | 29.81 | 26.26 | 29.03 | 26.01 | 26.74 | 26.54 | 28.19 | 28.245 |
| 5 d | 30.56 | 32.95 | 29.15 | 30.34 | 28.08 | 30.33 | 26.38 | 27.16 | 27.95 | 28.45 | 29.135 |
| 7 d | 31.92 | 34.78 | 29.72 | 31.92 | 29.02 | 31.8 | 27.25 | 28.97 | 30.06 | 30.59 | 30.603 |
| 9 d | 33.05 | 36.27 | 30.22 | 33.16 | 30.14 | 32.76 | 28.07 | 30.15 | 32.54 | 32.48 | 31.884 |
| 11 d | 34.65 | 37.94 | 30.87 | 34.57 | 31.56 | 34.75 | 28.89 | 31.6 | 33.99 | 34.73 | 33.355 |
| 13 d | 35.18 | 38.74 | 30.02 | 33.9 | 31.76 | 34.52 | 29.05 | 31.96 | 33.3 | 34.07 | 33.25 |

20 Kunming mice (half male and half male) were injected with sp2 at a dose of 2000 mg/kgBW through the tail vein. During the prescribed continuous observation for 14 days (including 0 days, a total of 14 days), no damage was found, including no obvious behavioral abnormalities, no weight loss, and no deaths. After the experiment, no tissue or organ abnormality is found after general dissection. Conclusion: the maximum non-toxic dose of sp2 administered intravenously is 2000 mg/kgBW.

For any person skilled in the art, without departing from the scope of the technical solution of the present disclosure, the technical content disclosed above can be used to make many possible changes and modifications to the technical solution of the present disclosure, or modified into an equivalent embodiment with equivalent changes. Therefore, all simple modifications, equivalent changes and modifications made to the above embodiments based on the technical essence of the present disclosure without departing from the technical solutions of the present disclosure should still fall within the protection scope of the technical solutions of the present disclosure.

The invention claimed is:

1. A method of treating cancer, enhancing anti-tumor immune response, inducing tumor cell differentiation, or inhibiting tumor telomerase activity, comprising administering an effective amount of a composition intravenously to a subject in need thereof, wherein the composition comprises a synthetic peptide sp2 consisting of the amino acid sequence of SEQ ID NO:1, wherein the subject is a human.

2. A method of enhancing anti-tumor immune response, regulating tumor cell cycle, inducing tumor cell differentiation, or inhibiting tumor telomerase activity, comprising administering an effective amount of a composition intravenously to a subject in need thereof, wherein the composition comprises a synthetic peptide sp2 consisting of the amino acid sequence of SEQ ID NO:1, wherein the subject is a human.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: artificial sequence
<220> FEATURE:
<223> OTHER INFORMATION: synthesized

<400> SEQUENCE: 1

Arg Val Leu Asn Gly Pro Glu Glu Ala Ala Ala Pro Ala Glu
1               5                   10                  15
```